(12) United States Patent
Wapner et al.

(10) Patent No.: US 6,458,231 B1
(45) Date of Patent: Oct. 1, 2002

(54) METHOD OF MAKING MICROTUBES WITH AXIALLY VARIABLE GEOMETRIES

(75) Inventors: Phillip G. Wapner; Wesley P. Hoffman, both of Palmdale, CA (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/274,820

(22) Filed: Mar. 17, 1999

(51) Int. Cl.⁷ ............................................. B65H 81/00
(52) U.S. Cl. ...................... 156/173; 156/175; 156/169; 428/36.3
(58) Field of Search ................................ 156/148, 155, 156/166, 169, 173, 175; 604/526, 527; 264/281; 428/36.3

(56) References Cited

U.S. PATENT DOCUMENTS

| | | | |
|---|---|---|---|
| 2,614,058 A | * 10/1952 | Francis | 154/83 |
| 3,879,516 A | * 4/1975 | Wolvek | 264/135 |
| 5,700,253 A | * 12/1997 | Parker | 604/282 |
| 5,704,926 A | * 1/1998 | Sutton | 604/282 |
| 5,879,499 A | * 3/1999 | Corvi | 156/175 |
| 5,947,940 A | * 9/1999 | Beisel | 604/282 |
| 6,030,371 A | * 2/2000 | Pursley | 604/282 |
| 6,059,001 A | * 5/2000 | Wapner et al. | 156/425 |

* cited by examiner

Primary Examiner—Jeff H. Aftergut
Assistant Examiner—Jessica Rossi
(74) Attorney, Agent, or Firm—Thomas C. Stover; Stanton E. Collier

(57) ABSTRACT

In the present invention, a technique is described for manufacturing microtube devices which have peripheral geometries that are not uniform along the tube or device axis. These geometries may exist in only one location on the periphery of the microtube device or geometries may be repeated either uniformly or non-uniformly with micron or sub-micron precision along the tube or device axis. The preferred manufacturing process involves forming a complex mandrel, ie., (one, for example, that can not be formed by extrusion or pultrusion under constant processing conditions) and giving it at least one metallic and/or non-metallic coating by any of a variety of techniques. The complex mandrel can then be removed by appropriate chemical or physical means that do not adversely affect the coating(s) desired for the wall. The result is a microtube structure having an axial profile duplicating that on the mandrel from which it was formed.

18 Claims, 22 Drawing Sheets

A

B

A

B

G
---
H

METHOD OF MAKING MICROTUBES WITH AXIALLY VARIABLE GEOMETRIES

CROSS-REFERENCES TO RELATED PATENT APPLICATIONS

The present patent application is related to U.S. patent application Ser. No. 08/472,574 now U.S. Pat. No. 6,059,001. Although the present patent application is not pending therefrom, it incorporates several features as shown and described therein.

STATEMENT OF GOVERNMENT INTEREST

The invention described herein may be manufactured and used by or for the Government for governmental purposes without the payment of any royalty thereon.

BACKGROUND OF THE INVENTION

The present invention relates to machines, and, in particular, relates to micromachines, and further, relates to free-standing microtube devices.

In recent years there has been tremendous interest in miniaturization due to the high payoff involved. One area of current interest is microelectromechanical systems (MEMS) and the closely related fields of micro-fluidics and micro-optical systems. Presently, these technologies involve micro-machining on a silicon chip to produce numerous types of devices, such as sensors, detectors, gears, engines, actuators, valves, pumps, motors, and mirrors on the micron scale. The first commercial product to arise from MEMS was the accelerometer manufactured as a sensor for air-bag actuation. On the market today, there are also micro-fluidic devices, mechanical resonators, biosensors for glucose, and disposable blood pressure sensors that are inserted into the body.

The vast majority of microsystems are made almost exclusively on planar surfaces using technology developed to fabricate integrated circuits. That is, the fabrication of these devices takes place on a wafer and the device is formed layer-by-layer with standard clean-room techniques that include e-beam or photolithography, thin-film deposition, and wet or dry etching.

Although there have been numerous and very innovative successes using these silicon wafer-based technologies, there are some disadvantages. Since it requires the building-up of many layers of different materials as well as surface and bulk micro-machining there are some very difficult material science problems to solve. These include differential etching and laying down one material without damaging a previous layer. In addition, there are the problems associated with interconnecting layers in a chip with different functions. An example of this would be a micro-fluidic device in which there are both fluidic and electronic functions. Clearly, there are numerous materials' issues central to this technology.

In addition to these processing problems, there are other limitations inherently associated with conventional lithographic techniques that are based on planar silicon. For example, in some applications such as those that involve surface tension in fluidics, it is important to have a circular cross-section. However, it is impossible to make a perfectly round tube or channel on a chip with current technology. Instead channels are made by etching a trench and then covering the trench with a plate. This process can only produce angled channels such as those with a square, rectangular, or triangular cross-section.

Thus, there exists a need for microtube devices not associated with planar technology.

SUMMARY OF THE INVENTION

In the present invention, a technique is described for manufacturing microtube devices which have interior geometries that are not uniform along the tube or device axis. These geometries may exist at only one location along the axis of the microtube device or specific geometries may be repeated either uniformly or non-uniformly with micron or sub-micron precision along the tube or device axis. The preferred manufacturing process involves first forming a complex fiber mandrel. {In this application we define a complex fiber mandrel as one that can not be formed by extrusion, pultrusion, spinning, stretching, or drawing (with or without a die) under uniform fabrication conditions that do not vary with time.} Once the complex fiber mandrel has been formed, it is given at least one metallic and/or non-metallic coating by any of a variety of techniques. The complex fiber mandrel can then be removed by appropriate chemical or physical means that do not adversely affect the coating(s) desired for the tube wall. This results in a microtube structure having an interior axial profile duplicating the exterior profile on the mandrel from which it was formed. The microtube structures of this application as well as the microtubes and microtube devices of previous patents can stand alone or can be a component part of another device.

One group of techniques for forming a complex mandrel consists of employing non-uniform conditions while making fibers using techniques normally employed in the production of fibers. Another group of techniques for forming the complex mandrel consists of adding material to, removing material from, or redistributing material on a fiber core at precise locations on the periphery of the fiber core, which consists of one or more fibers held rigid during processing. The term fiber as used here is used in its most general sense and refers to natural or synthetic filaments of any material such as polymer, cellulose, glass, ceramic or metal. In the case of material addition to the fiber core, the added material may be of the same composition as the fiber core or of a different composition. An additional type of technique for forming a complex mandrel involves wrapping at least one threadlike component around a core. These overwrap threadlike components may be of the same composition as the core or they may be of a different composition. In the simplest example both the core and the overwrapped threadlike component are as-extruded or as-drawn fibers. However, it should be noted that in some applications the core can also be a macroscopic object with a threadlike component, microtube, or microtube device wrapped around it.

To form a complex mandrel by the wrapping of one fiber around another involves drawing a single core fiber (or bundle of core fibers) through a confining orifice. The overall fiber core is held with minimal constraint (typically by friction), so that no breakage takes place as it is drawn through the orifice. However, enough constraint exists so that torque applied tangentially by an overwrapping fiber (or fibers) as it is being wound around the fiber core does not cause the one or more core fibers to slip in the direction of applied torque. Moreover, the overwrapping one or more fibers must be wound sufficiently close to the constraining orifice that twisting of the core one or more fibers in the direction of torque is minimized to such an extent that unwinding, or "backlash" does not occur when constraining forces are removed at the end of winding. Also, sufficient force must be exerted by the overwrapping fiber to insure that it winds itself tightly around the fiber core, thereby precisely maintaining desired dimensions and geometry. Finally, physical properties of the overwrapping fiber must be such that torsional stresses remaining after winding are insufficient to disrupt configuration of the formed mandrel when constraining forces of the winder are released. Polyetherimide has been found to be an excellent overwrapping fiber in this respect.

Therefore, one object of the present invention is to provide several methods for making complex fiber mandrels.

Another object of the present invention is to provide a precision-controlled adjustable-torque micro-winder able to wind one or more micron-sized fibers around a core of a micro-object, macro-object, or at least one micron-sized fiber.

Another object of the present invention is to provide a method of making microtube devices from complex mandrels.

Another object of the present invention is to provide a variety of microtube devices.

These and many other objects and advantages of the present invention, will be readily apparent to one skilled in the pertinent art from the following detailed description of a preferred embodiment of the invention and the related drawings.

DETAILED DESCRIPTION OF THE PREFERRED EMBODIMENT

Figure 1:
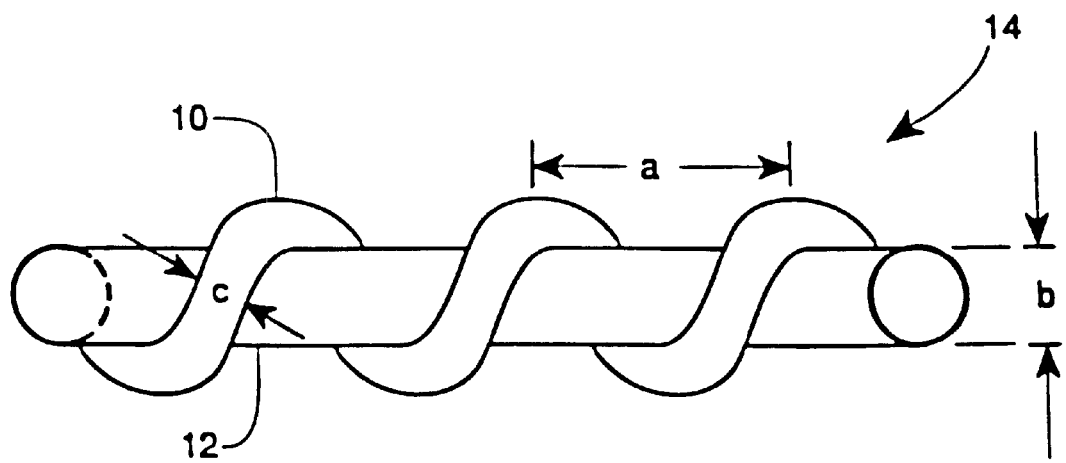
FIG. 1 illustrates a fiber wrapped around a core fiber.

In the present invention, a technique is described for manufacturing microtube devices which have interior geometries that are not uniform along the tube or device axis. These geometries may exist at only one location along the axis of the microtube device or specific geometries may be repeated either uniformly or non-uniformly with micron or sub-micron precision along the tube or device axis. The preferred manufacturing process involves first forming a complex fiber mandrel. {In this application we define a complex fiber mandrel as one that can not be formed by extrusion, pultrusion, spinning, stretching, or drawing (with or without a die) under uniform fabrication conditions that do not vary with time.} Once the complex fiber mandrel has been formed, it is given at least one metallic and/or non-metallic coating by any of a variety of techniques. The complex fiber mandrel can then be removed by appropriate chemical or physical means that do not adversely affect the coating(s) desired for the tube wall. This results in a microtube structure having an interior axial profile duplicating the exterior profile of the mandrel from which it was formed.

The term complex mandrel as used in this application is a general term used to describe at least one fiber or microscopic object of high aspect ratio of length to diameter whose axial profile is not uniform. That is, there can exist protrusions, depressions, or changes in radial dimensions of any desired shape and location on the periphery of the complex mandrel. Thus, these complex mandrels, which have any desired cross-sectional shape, can possess either a uniform, non-uniform, or random variation in thickness at any point along their axes. Complex mandrels consist of a core of at least one fiber or at least one microscopic object of high aspect ratio with a cross-sectional dimension in the range of 1–1000 microns. When the axial profile varies due to a change in radius of the core, this type of mandrel is called a complex radial mandrel. If the axial geometry is modified by adding material of desired shape and height at predetermined locations on the periphery of the fiber core, the complex mandrel is called a complex augmented mandrel. In contrast, a complex reduced mandrel is formed by selectively removing material to a desired depth from the periphery of the fiber core at pre-determined locations. Movement of material on the fiber surface to produce the desired axial geometry is called a complex redistributed mandrel. Additionally, the axial geometry of a core can be modified by overwrapping at least one threadlike component around the core. The resulting complex mandrel is called a complex overwrapped mandrel. Finally, if more than one of these techniques is employed sequentially on any one mandrel, the resulting mandrel is referred to as a complex sequential mandrel.

As just mentioned, one technique for forming a complex mandrel consists of changing the radial dimension along the axis of the fiber core. There are many ways to do this in either a random, uniform, or non-uniform fashion. For example, the radius of a fiber can be changed during manufacture by changing the manufacturing parameters as the fiber is being made. Taking melt spinning of fiber as an example, the radius of the fiber can be changed by varying one or more parameters such as, the temperature of the melt, the pressure on the melt, the local fiber density, the tension on the fiber, the geometry of the spinnerette or the geometry of the spinning process itself. With wet spinning, there is the additional possibility of varying the composition of the fiber or the solution. The change in the radius along the axis could be a single event or cyclic. In addition the change could be random, uniform, or vary in a predictable manner with location along the fiber axis.

The radius of a fiber or a coated fiber can also be changed after it has been manufactured. For example, the radius of a hollow fiber can be increased either randomly, uniformly, or non-uniformly at any desired location(s) along the fiber axis using heat and pressure or a combination of these parameters. For example, using a combination of heat and differential pressure (higher internally), the diameter of a hollow fiber that softens with temperature can be increased at the position where heat is applied. Depending upon how uniform the heat and differential pressure are applied at each point along the axis structures such as bubbles and tapers can be fabricated. In addition, the radius of a fiber can be decreased either randomly or uniformly using heat, tension, pressure or a combination of these parameters. For example, using a combination of heat and tension, the diameter of a fiber that softens with temperature can be decreased. Depending upon how uniform the heat and tension are applied at each point along the fiber axis a myriad of structure from tapers to teardrops can be fabricated. It should be noted that this is the only technique discussed in this application where the length of the mandrel core changes. In addition, it should be noted that with these techniques that vary the radius along the axis, the radius around the axis at each position along the axis may or may not be uniform depending upon how uniformly the heat, for example, is applied.

Another technique for forming a complex mandrel consists of winding at least one threadlike component with a cross-sectional dimension in the range of 1–1000 microns around a core. In one preferred embodiment of this technique discussed in the examples that follow, this core consists of at least one fiber. However, it should be noted that the core can also be any microscopic object of relatively high aspect ratio of length to diameter with a dimension in at least one direction of 1–1000 microns. Likewise, in one preferred embodiment of this technique discussed in the examples that follow, the threadlike overwrapping component consists of at least one fiber. However, it should be noted that the threadlike component cab also be any microscopic object of relatively high aspect ratio with dimension in at least one direction of 1–1000 microns.

In light of the foregoing discussion, it needs to be recognized that either the core, the threadlike overwrapping component, or both can consist of at least one axially uniform fiber, a microscopic object of relatively high aspect ratio, another complex mandrel, a coated complex mandrel, a complex mandrel from which the core, or mandrel and/or at least one coating has been removed, or even a complex sequential mandrel that has been previously manufactured.

In one preferred embodiment using a fiber as the core, the fiber is drawn through a confining orifice in a precision-controlled adjustable-torque micro-winder. The fiber is held with minimal constraint (typically by friction), so that no breakage takes place as it is drawn through the orifice. However, enough constraint exists so that torque applied tangentially by another overwrapping fiber (or fibers) as it is being wound around the fiber core does not cause the core fiber(s) to slip in the direction of applied torque. Moreover, the overwrapping fiber must be wound sufficiently close to the constraining orifice that twisting of the fiber core in the direction of torque is minimized to such an extent that unwinding, or "backlash" does not occur when constraining forces are removed at the end of winding. Also, sufficient force must be exerted by the overwrapping fiber to insure that it winds itself tightly around the fiber core, thereby precisely maintaining desired dimensions and geometry. Finally, physical properties of the overwrapping fiber must be such that torsional stresses remaining after winding are insufficient to disrupt configuration of the formed mandrel when constraining forces of the winder are released. Polyetherimide has been found to be an excellent overwrapping fiber.

In all areas of science and engineering, as miniaturization has occurred, some physical and chemical effects and parameters have either become dramatically elevated in importance or actually become the dominant variables. In a very real manner of speaking, new worlds are entered into, in which design considerations and forces that are normally negligible in human-scale applications become essential to successful utilization and application of the miniaturized technology. What makes the precision-controlled adjustable-torque micro-winder used in this invention to make complex microtube mandrels uniquely different from a much larger-scale winding apparatus is that it specifically addresses these micro-effects. In a larger macro-scale winder, overwrap torques due to fiber winding position and fiber physical properties are either negligible because overwrap wires or cables are much smaller or weaker than the core, or the overwrapping process is made torque-balanced with respect to the core by wrapping two or more wires or cables simultaneously on the core from either multiple or simply opposing directions, thereby eliminating any net torque in only one direction on the core. This latter process usually requires that the core remain stationary with the overwrapping wires or cables being rotated about it in order to perform wrapping. In this winder, however, because of the micro-scale, the ability to precisely adjust and control net torque on the core by the at least one overwrapping fiber is critical to successful fabrication of microdevices of the present invention.

Referring to FIG. 1, actual winding of the overwrapping fiber(s) 10 around the fiber core 12 can be accomplished in numerous ways. The three most useful are: (1) rotating the fiber core 12 as it is drawn through the orifice, while not allowing the overwrapping fiber to rotate, but only to translate along its axis towards the fiber core under controlled tension; (2) holding the fiber core non-rotating as it is drawn through the orifice, and the overwrapping fiber wound around it under tension; and (3) rotating both core and overwrapping fiber either in the same or opposing directions during winding with the result being a braided or woven overwrap.

Spacing of the wound overwrapping fiber(s) on the fiber core is accomplished by controlling the number of complete overwrap-windings allowed to occur per unit displacement of the fiber core away from this orifice. If core displacement and overwrap rotation rates are held at a preset value, a helical winding as seen in FIG. 1 will result which will have axial spacing dependent on the actual rates involved. If either core displacement or overwrap rotation rates are allowed to vary, much more complex axial repeat units, or geometries on the complex overwrapped mandrel, can be generated. Under suitable conditions, no repeat units will exist. However, the resulting winding profile will be reproducible as long as the same rotation-rate patterns are employed. It is also possible to allow the fiber core to reverse direction; i.e., draw it back into the constraining orifice. This will result in over-winding of the overlap fibers on themselves.

In utilizing winding to make complex mandrels, there are numerous ways of actually winding overwrapping fibers over the fiber core. One type of winding apparatus 16, depicted in FIGS. 2, 3, and 4, has been constructed and used to make complex overwrapped mandrels which, after coating and core or mandrel removal, produced microbellows, microsprings, and microscrews, among other products. The winding apparatus 16 consists of two rotating gripping vises 18, whose motion is coordinated by a sliding actuator 20. This actuator 20 consists of one noncircular tube 22 shaped to smoothly fit inside another similarly-shaped tube 24, both mounted in drive wheels 26 and 28, causing rotation of each vise. This synchronizes rotary motion of both vises, yet permits linear translation of the second, or "locking" vise 30, that holds and pulls the accompanying fiber core. The other vise, or "pull-through" vise 32 does not translate linearly. Spring-loaded jaws 33, shown in FIG. 3, centrally located in each vise have adjustable screw mechanisms. These jaws allow the locking vise to hold the fiber core tightly, completely preventing any slippage. Simultaneously, jaws in the pull-through vise are able to grasp the fiber core with just enough force to ensure rotary motion precisely in step with the vises, yet gentle enough to allow smooth fiber pull-through without elongation. FIGS. 3 and 4 illustrate the overwrap positioning device 34 which is positioned closely to the pull-through vise 32. It consists of a slotted guide 36 which feeds overwrap fibers 10 over a pulley 35 to the rotating fiber core 12 using the weight of the fiber and an additional weight 38 attached to the overwrap fiber 10 as a tensioning mechanism. The positioning-device spacing 37 must be close enough to the pull-through vise to eliminate twisting of the fiber core in the direction of applied overwrap torque. This also requires careful balancing of overwrap tensioning weight. Too little weight, and overwrap fibers will not wind tightly leaving gaps. Too much weight, and the fiber core will twist no matter what positioner spacing is used. When constraining forces supplied by the vise jaws are removed at the end of overwrapping, any unwinding resulting from the fiber core twisting will destroy the fabricated micro-mandrel.

In fabricating complex overwrapped mandrels with the precision-controlled adjustable-torque micro-winder, the core and overwrap fibers can be but do not have to be of the same material, same cross-sectional shape or dimension. For some applications it is desirable that at least one fiber or microscopic object of high aspect ratio in the core be coated with at least one coating before over wrapping the at least one threadlike component. In addition, the one or more overwrap threadlike components can also be coated with at least one suitable material either prior to winding or after winding to increase their bonding to the fiber core, to fill in gaps and/or crevasses between fibers, or for special microtube manufacture. It is also possible to melt the surface of the one or more overwrap threadlike components prior to winding over the fiber core so that their position is secured by a melt-bond.

Once the complex overwrapped mandrel has been fabricated, it can be coated with at least one layer of material and then the mandrel can be removed by a process that does not adversely affect the one or more coatings. The result is a microtube device with variable axial geometry.

As with all the processes discussed in this application there are numerous variations to the basic process just described. For example, a coated complex mandrel can be overwrapped with at least one threadlike component to increase the wall strength of the device. This overwrapped threadlike component, which can be bonded to the mandrel coating, could then have at least one additional coating deposited on top of it if desired. (Alternatively, of course the overwrapped at least one threadlike component could be coated before it was wrapped.) If the overwrapped threadlike component is then removed from the coating, a microtube device with an overwrapped tube would result.

Another variation to the process just described produces a microtube with a complex wall. In this case, instead of overwrapping an un-coated core forming a complex mandrel and then coating it, a core consisting of at least one fiber or microscopic object of high aspect ratio of length to diameter is coated with at least one coating not adversely affected by the conditions needed for the removal of the core. This coated core is then overwrapped with at least one fiber or at least one threadlike component either in a single or multiple passes to produce a wrapped or braided coated-core. Another coating that is not adversely affected by the removal of the core is applied on top of the overwrapped coated-core. When the core is removed, a microtube with a complex wall is produced. Of course, this process of overwrapping and coated can be repeated as many times as needed for the particular application. With the fiber or threadlike component remaining in the wall, a microtube with a reinforced wall is produced. If the fiber or threadlike component in the wall is subsequently removed by a process that does not adversely affect the coatings, a central microtube with another microtube wrapped around it is produced. This same device could also be produced by overwrapping the core with a threadlike component that had previously been coated.

A variation of the process to fabricate a microtube with a reinforced wall involves coating the core with a thick coating and then embedding the overwrapped fiber in this coating. This can be accomplished in several ways such as using a hot wire as the overwrapping fiber or by softening the coating before overwrapping.

A final variation of the overwrapping of a threadlike component around a core to be mentioned involves the size of the core. In addition to the microscopic cores mentioned thus far in connection with the precision-controlled adjustable-torque micro-winder, it is also possible to overwrap an object larger than 1000 microns with a fiber or thread-like component, coated fiber or coated thread-like component, or a microtube using a more conventional winding machine. In addition, this larger core can also be overwrapped with a complex mandrel, coated complex mandrel, complex mandrel from which the core, or complex mandrel, and/or at least one coating has been removed, complex sequential mandrel, coated complex sequential mandrel, or a complex sequential mandrel described below from which the core, complex sequential mandrel, and/or at least one coating has been removed. In this variation, the larger core can be formed from a complex sequential mandrel discussed below or could be any other object in the range of 1000–25000 microns. The over-wrapped core is called a complex overwrapped macro-mandrel and a microtube device with at least one internal dimension less than 1000 microns that has been formed from a complex overwrapped macro-mandrel is called a macro-sized microtube device. After overwrapping the core, it can be removed or remain. Subsequent processing may involve additional coating and removal cycles as required for the particular device.

Obviously, in overwrapping a threadlike component around a core, there are only two degrees of freedom that are needed. The core must translate and rotate with respect to the feed position of the at least one overwrapping threadlike component. This can be accomplished as in the present example by both translating and rotating the core. Equivalent complex mandrels can also be fabricated by rotating the core and translating the overwrapping positioning device 34 along the axis of the core, translating the core and rotating the overwrapping positioning device 34 or by both rotating and translating the overwrapping positioning device 34 with respect to the core. However, no matter how the threadlike component is overwrapped around the core, the types of complex mandrels that can be formed are limited by the fact that an overwrapping threadlike component is being used which by necessity is a continuous process around each core.

There are many other techniques discussed below that are able to add material to, remove material from, or move material on a fiber core in either a continuous or a non-continuous manner and thus are able to produce additional types of complex geometries. These other techniques require the use of a multi-axis complex microtube mandrel fabrication device with micron, or even sub-micron, positioning capability. This device, which in one configuration is essentially a more versatile and sophisticated form of the precision-controlled adjustable-torque micro-winder described above, can take a multitude of forms. Basically it is comprised of a head that takes the place of the overwrapping positioning device 34. This head is able to continuously or non-continuously add material to, remove material from, change material on, or move material on a fiber core, which is held straight in a fixture. Like the precision-controlled adjustable-torque micro-winder there must be relative translational and rotational motion between the head and the fiber core. (This can obviously be accomplished in many ways as described above but for the purpose of the examples that follow it is assumed that the fiber core will both rotate and translate with respect to a stationary head.) In addition, for some techniques, there needs to be additional degrees of freedom for alignment of the head with respect to the fiber core. Thus, there needs to be the ability in many applications to move the head orthogonally in up to three dimensions with respect to the fiber core so that material is added, removed, changed or moved at the right position on the fiber core. In most applications the head is aligned perpendicular to the fiber core axis but for some applications tilt of the head with respect to the fiber core axis will also be needed so that material is added or removed at the desired angle to the fiber core.

Complex mandrels formed by adding material to the fiber core are called complex augmented mandrels. These mandrels are formed by putting a fiber core composed of at least one fiber in a multi-axis complex microtube mandrel fabrication device and then placing at least one type of material with a predetermined cross-sectional shape on the fiber core in at least one predetermined location on the periphery of the fiber core. The placement of material can be either in a continuous or non-continuous manner. In addition, more than one pass, with the same or different material, can be made at each location on the surface of the fiber core so that the desired thickness of material can be placed. Thus, it is possible not only to control the position of material placement on the surface but also the type or types of material at each location on the periphery of the fiber core.

Once the desired complex mandrel has been formed it is coated with at least one layer of material producing a coated complex augmented mandrel. If it is desired to produce a microtube device with the interior shape of the complex mandrel, the coating or coatings should not be removed by the process used to remove the complex augmented mandrel after it has been coated.

A technology capable of forming complex mandrel geometries by adding material to the fiber core is melt extrusion. In this technique material is melt extruded directly onto the core in a circumferential and/or axial manner. The head of the multi-axis complex microtube mandrel fabrication device for this technique consists of a very small diameter orifice or microscopic tube connected to a reservoir of molten material under pressure. For purely circumferential melt placement, translation of the core is halted but its rotation is continued. In contrast, for purely axial melt placement on the core, rotation is halted, but translation allowed to continue. It should be noted that there are numerous combinations of these two elementary processes in conjunction with the ability to control the flow of molten material, which can be used to produce complex mandrels with either uniform or random geometries after the viscous molten material has solidified. Also, it should be mentioned that with this technique, as with all the others described in this application, complex mandrels formed in this manner, in addition to being coated to form devices after the complex mandrel is removed, can also be used as the core (either coated or uncoated) in subsequent processing. In this manner, a vast number of non-circular core-fiber cross-sections can be fashioned from either a circular or non-circular fiber core in a sequential process. These melt-processed non-circular core-fiber segments can be interspersed at will between either repeat wound segments or other repeat melt-processed non-circular core-fiber segments with different geometry. It is also possible to make a microtube mandrel with this technique that has no repeat units, only a geometry that varies both circumferentially and/or cross-sectionally in a predetermined fashion.

A variation of the melt extrusion process to form a complex augmented mandrel with the desired topography is to selectively place a viscous liquid of desired cross-sectional shape, such as a monomer or polymer, on the surface of the core in any desired manner. After the viscous liquid is placed on the surface at the desired positions, it can be dried if necessary by removing any solvent. If it is a monomer or polymer, curing or polymerization of the monomer or further cross-linking of the polymer using, for example, an energetic particle beam (for example, electrons), temperature or radiation can be performed to produce a solid rigid topography on the surface of the core.

A vapor-phase process for forming complex augmented mandrel geometries is also useful. Techniques such as plasma spraying either through appropriate "masks" or using microscopic nozzles can be employed to place deposited material on the core. Other types of chemical or physical vapor deposition, such as, magnetron sputtering can also be employed using a masking technique to selectively deposit one or more material on the surface.

A second class of technologies useful for forming complex mandrel geometries is conceptually the opposite of the previous mandrel-forming techniques discussed, in that rather than adding material in order to form a particular geometry on the core surface, it selectively removes material from a core or core coating, either in a circumferential and/or axial manner to produce a complex reduced mandrel. A rotating and/or translating core or coated core held in a multi-axis complex microtube mandrel fabrication device can have material "trimmed" either by energy (i.e., electron, ion, laser) beam ablation or other non-contact high-energy-delivery process (EDM for example), by particulate impact such as with a micron or sub-micron-sized particulate (sand, silicon carbide, alumina, etc.), or by using heat, such as in the form of a micro-heatgun with a microscopic tube or orifice, or a hot wire. All these ablation techniques can be performed using either a focused beam of particulates, energetic particles, ions, or radiation by themselves or in conjunction with a mask between the core and a source of particulates, energetic particles, heat, ions, or radiation. By appropriately controlling core rotation and translation, as well as location of the ablating beam or heatgun relative to core axis, any of the complex mandrel geometries obtained with material deposition processes discussed previously as well as other geometries can be produced.

Alternatively, at least one fiber in the core can be coated, for example by dipping or spraying followed by rotation about the fiber axis to even out the coating as it solidifies if this is desired. It is then possible to selectively remove some or all of this material at precise locations on the fiber core periphery. It is certainly possible to selectively remove some of this coating using the techniques just described. However, another preferred embodiment is to coat at least one fiber in the core with a material such as photoresist (either positive or negative). After coating, the fiber is exposed to radiation or a particle energy source that will develop some of the photoresist and produce the desired topology on the surface of the fiber after some or all of this exposed material or the unexposed material at precise locations on the fiber core periphery is selectively removed, for example, by solvation or plasma. This exposure of the photoresist can be performed through a mask as is traditionally done in 2-D lithography or it can be done using a focused radiation or particle source in combination with relative motion between the fiber and the radiation or particle source. In one application, the head of the complex microtube mandrel fabrication device would consist of either a focused radiation or particle source and in the other application it would hold the mask. Obviously, for these applications in addition to the need for the head to be aligned relative to a position on the core, it is also necessary to be able to control the distance between the head and the core in order to properly focus the energy on the surface to produce a high quality complex reduced mandrel. As stated previously, to make a microtube device from the reduced mandrels, it is necessary to coat the mandrel with at least one layer of material that is not removed by the process used to remove the mandrel. This is called a coated complex reduced mandrel. Thus, when the mandrel is removed from the coating, a microtube device is formed.

Finally, in addition to depositing material on or removing material from the fiber core or a fiber core coating, the desired topology on the periphery of a core or coated core can be obtained by using techniques that move or redistribute material on the surface of the core or coated core to produce a complex redistributed mandrel. This movement of material occurs in either a continuous or non-continuous manner in at least one pre-determined location on the periphery of the core. In addition, more than one pass can be made at each location on the surface of the core so that the desired thickness of material can be redistributed.

The movement of material on the periphery of the core can be accomplished in many ways such as embossing using pressure either in a mold or a press, embossing with heat such as with a hot wire or heat source in combination with a tool used for pushing or pulling material, or by selectively crimping portions of the surface.

Five different means to form a complex mandrel (adding material to, removing material from, moving material on, changing the radial dimensions of, or wrapping around a core) have just been described. Each of these individual processes is able to produce a complex mandrel that can be coated and then removed producing a microtube device. However, it is also possible to use these complex mandrel fabrication techniques in sequence to produce even more elaborate complex mandrels called "complex sequential mandrels" that can not be produced in any other way. This sequential processing, which can involve any combination of processing in any order, is a 3-dimensional analog to commercial silicon wafer technology where there are many sequential steps to produce complex structures with many layers.

Thus, any product of one of the five complex microtube fabrication techniques which we call a "previously fabricated component" can be used as the core for subsequent processing with the same or a different process. Alternatively, they can be used as the overwrapping threadlike component in fabricating a complex sequential overwrapped mandrel. These previously fabricated components can be complex mandrels, complex mandrels that have been coated, or coated complex mandrels from which the core, or complex mandrel, and/or at least one coating has been removed. Thus, any product of a previous process can be used as a core or overwrapping threadlike component in one or more subsequent processes, which may be a different process or a repeat of the same process.

Since these complex sequential mandrels cab be formed in a number of ways it is convenient to name them by the last technique performed on them. Thus, for the sake of clarity, a core composed of at least one previously fabricated component that has material added to the core is called a complex augmented sequential mandrel. If material is removed from the core composed of at least one previously fabricated component, the result is a complex reduced sequential mandrel. If material is moved on the surface of the core composed of at least one previously fabricated component, the result is a complex redistributed sequential mandrel. Finally, if the core or the overwrapped threadlike component is composed of at least one previously fabricated component, the mandrel is called a complex overwrapped sequential mandrel. Obviously, this sequential processing can go through many cycles with the product of a previous process becoming the core or the overwrapped thread-like component of the present process.

As has been stated, in all the different techniques described in this present application that are used to produce a complex mandrel, either the core is moved relative to the head or the head is moved relative to the core. Obviously, numerous different types of complex microtube mandrel fabrication devices can be constructed so that any of the relative motions is possible. However, using the microwinder previously described, it is only possible to rotate and translate the fiber core relative to the stationary head.

Figure 2:
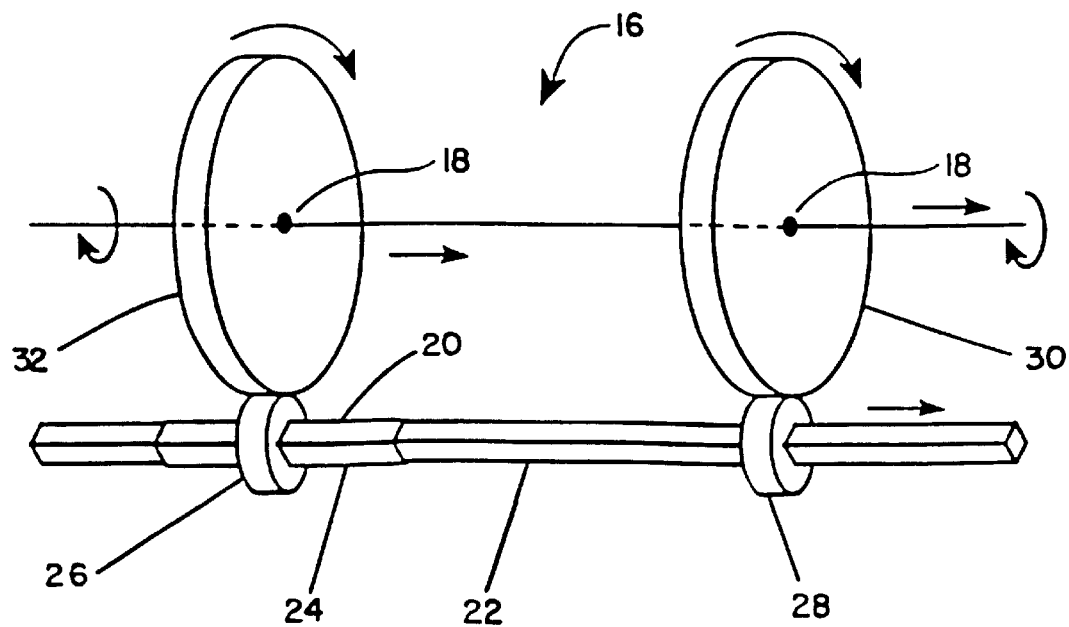
FIG. 2 partially illustrates a device for winding a fiber about a core fiber.
Figure 3:
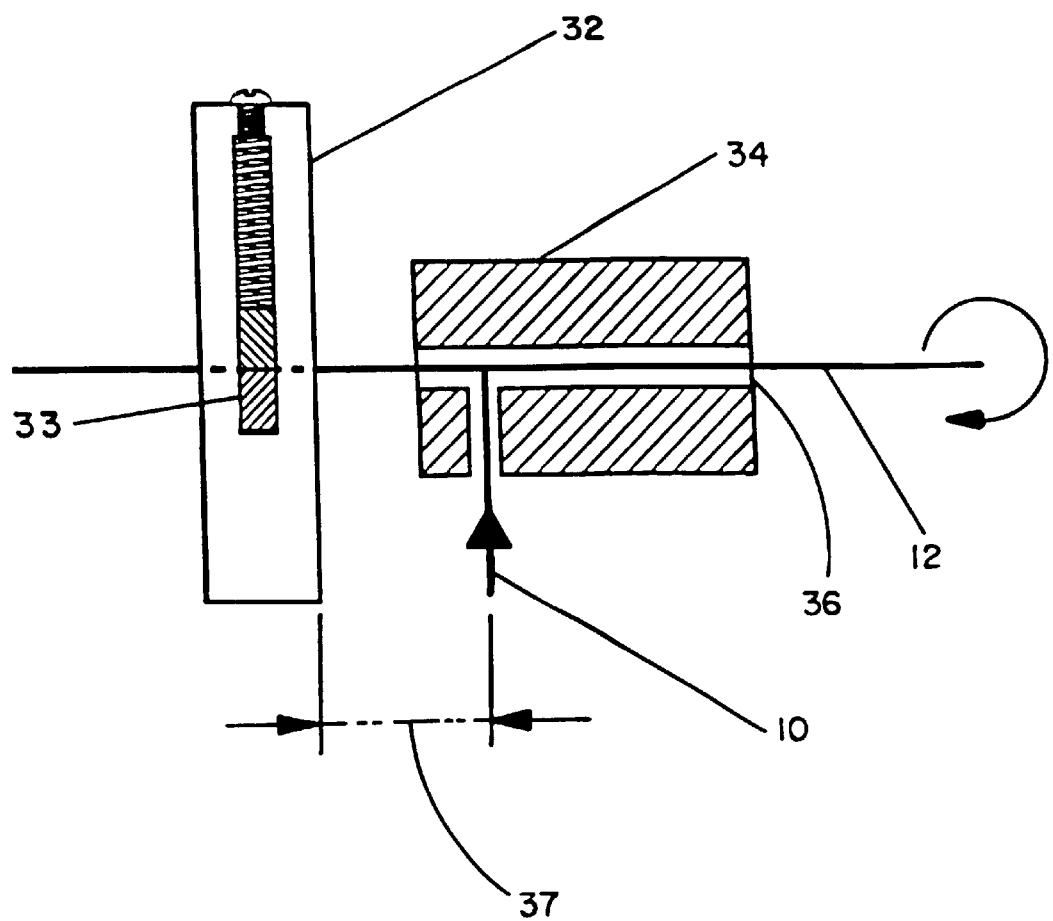
FIG. 3 partially illustrates a device for winding a fiber about a core fiber using a positioner.
Figure 4:
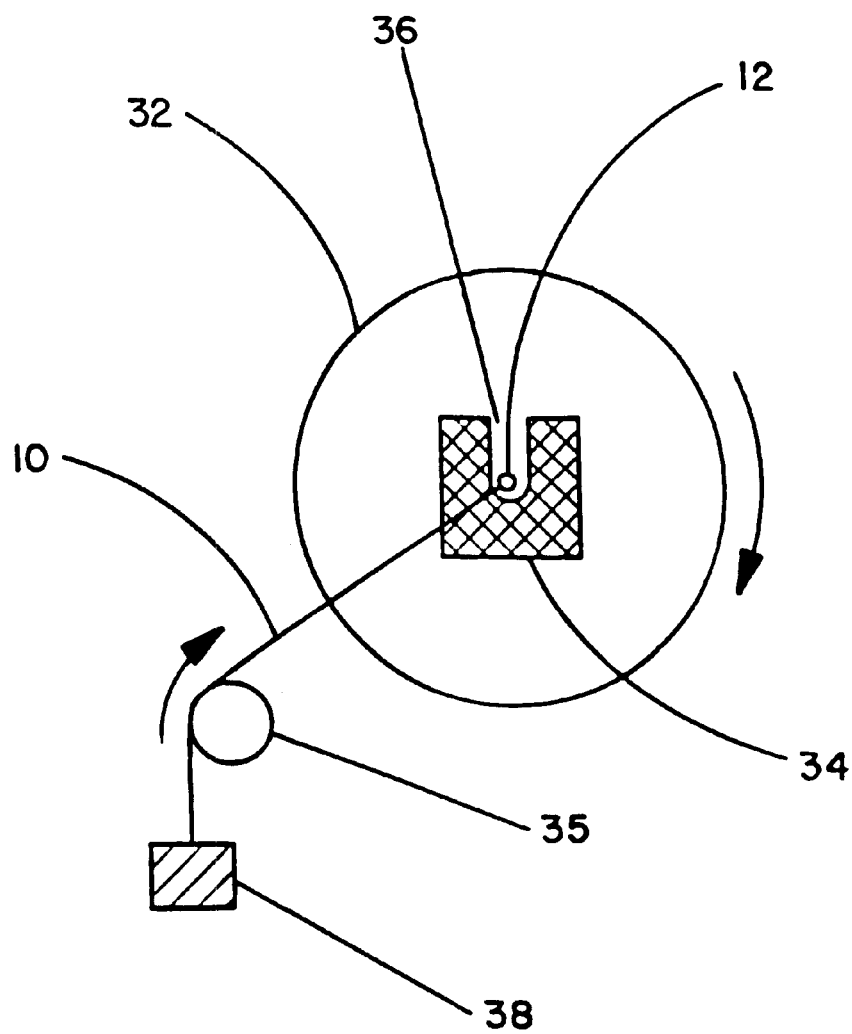
FIG. 4 is an axial view of the device of FIG. 3.
Figure 5:
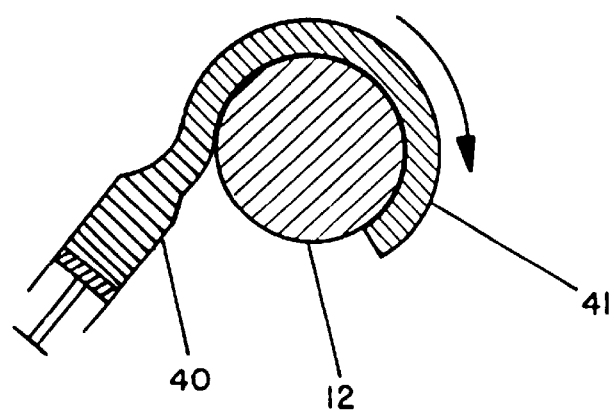
FIGS. 5A and 5B illustrate different methods of making structures with axial repeat unit.
Figure 5:
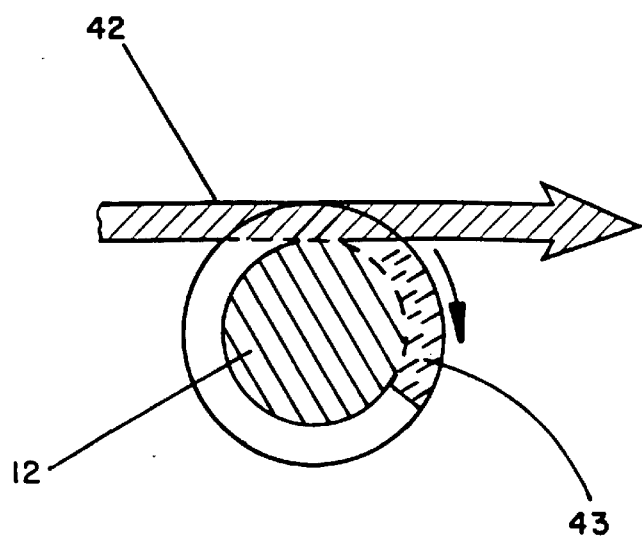

FIG. 5 illustrates how the basic winding apparatus depicted in FIGS. 2, 3, and 4 can be modified to enable melt or solution-processing, vapor-processing, ablation-processing and some forms of material movement to be performed. Essentially all that needs to be done is to replace the positioner 34 and accompanying overwrap fiber and overwrap weight with new devices capable of carrying out each particular mode of processing. For melt or solution-processing, a miniature polymer extruder similar in concept to a hot hypodermic syringe 40 delivers molten or solvated periphery modification material 41 to the rotating translating core fiber 12. For vapor-processing, a miniature plasma spray torch delivers periphery modification material material. And for ablation-processing, a suitable high-energy delivery system such as a radiative or particle beam 42 can be positioned in such a fashion that it "trims" unwanted material 43 from the rotating translating fiber core 12. In some applications, the high energy delivery system can be positioned to impact the unwanted material head-on, thereby cutting the unwanted material or the boundaries of the unwanted material at a high rate to facilitate removal. Alternatively, the head-on impact of the beam can be employed to modify the fiber core 12, for example, by making depressions or trenches in a solid core or by making holes or slits in a hollow core.

Although these processes are quite different from overwrap fiber winding, they too must be designed so that tensions and stresses, thermal as well as mechanical, induced by each type of process are carefully controlled-otherwise unacceptable distortion of the mandrel will take place either upon release from the basic winding apparatus or upon subsequent processing. As mentioned previously, this precision-controlled adjustable-torque micro-winder and its accompanying technology differs fundamentally from similar, but macroscopic, applications. Forces and effects usually considered negligible in macroscopic terms become over-riding at the micron level. For example, overwrap stress-strain properties are inconsequential in macroscopic winding applications. At the micron level, however, stress-strain behavior cannot be so easily dismissed. It is integral to successful fabrication.

The most straightforward devices capable of being manufactured with this process are bellows, springs, screws, heat exchangers, and 3-dimensional objects of revolution having dimensions on the micron level. Utilization of such miniature mechanical apparatus requires considerable innovation on the part of design engineers. Downsized applications range from flexible electrical connectors for micro-circuitry to novel new sensors utilizing microspring or microbellows displacements as a means of measuring applied force.

EXAMPLE 1

The simplest winding pattern is that of a helix 14, FIG. 1; i.e., a circular overwrap threadlike component 10 of diameter "c" wound around a circular core 12 of diameter "b", with a spacing of "a". The winding can be either right-handed or left-handed helix 14, and spacing can vary from a minimum of "a" equal to "c" to "a" approaching infinity. Both the core and the overwrapping threadlike component can be either a microscopic object of high aspect ratio or a fiber with a cross-sectional dimension in the range of 1–1000 microns. For the purposes of this example they are both assumed to be fibers.

Figure 6:
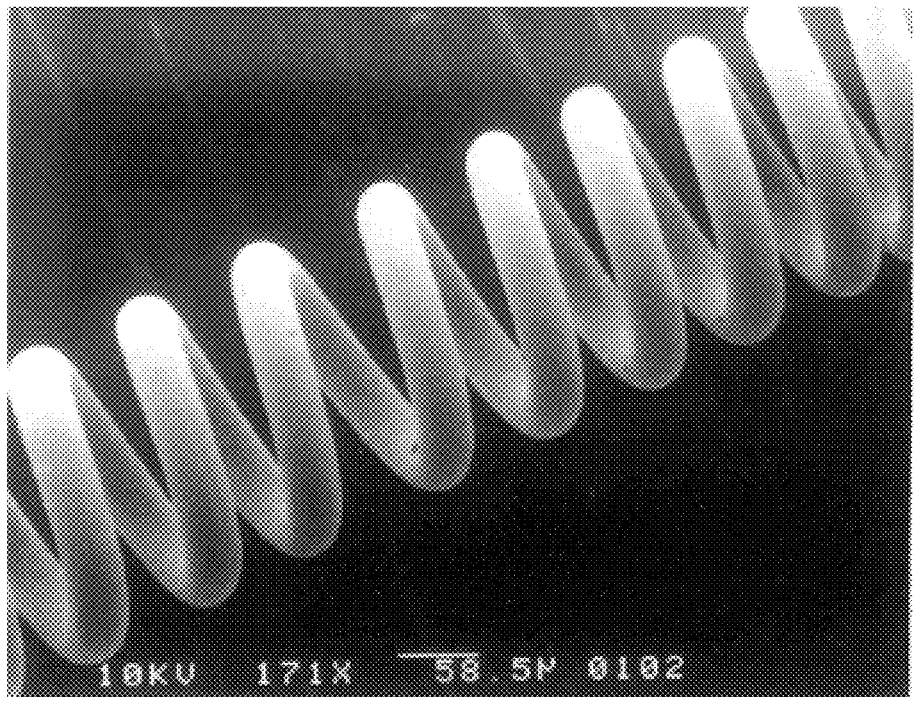
FIG. 6 illustrates a composite coil consisting of a coiled coated core fiber.
Figure 7:
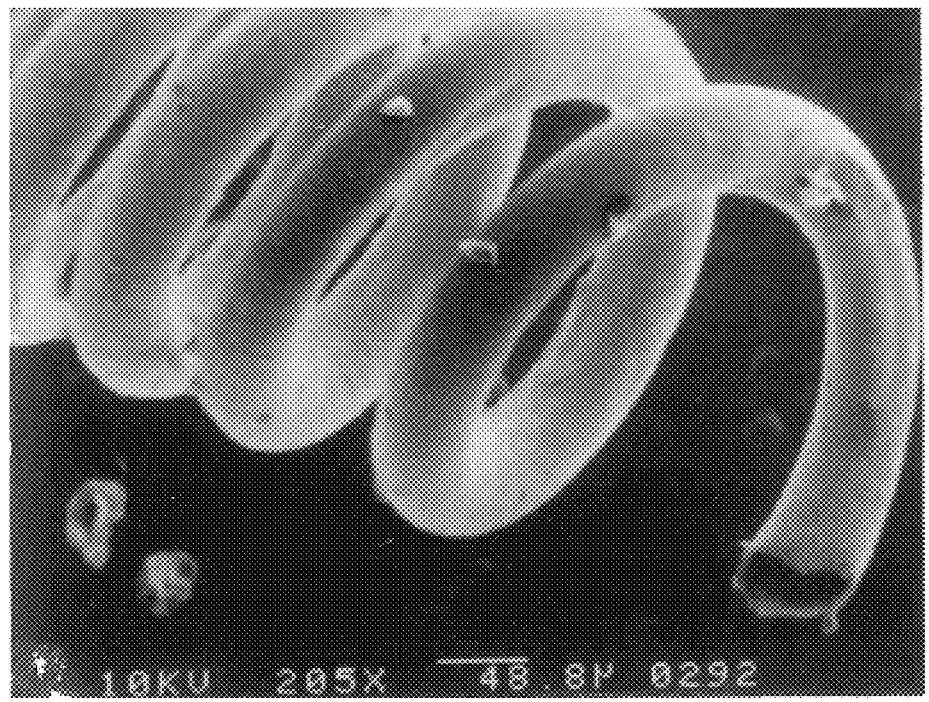
FIG. 7 illustrates a microtube coil.

If an overwrapped fiber is wound around a fiber core of unrelated materials that utilizes removal methods that have no adverse effect on the overwrapped fiber, then when the fiber core is removed, a coiled fiber will result. The method of removal of the fiber core in this example, which can for example be by reaction, solvation, vaporization, phase change, or simply pulling it out, is irrelevant to the formation of the coil. Once the coil is formed and free-standing, it is coated with the desired material. Of course, it is equally possible to coat the overwrapping fiber or threadlike component before it is wrapped around the core. If the coated overwrapped fiber is not removed from the coating, a composite coil is produced. as seen in FIG. 6. If the coated wrapped fiber is removed from the coating, a microtube coil is produced FIG. 7. These hollow coils can be used as a flexible coupling in microfluidic devices, a force or pressure sensor, or in electrical or magnetic applications such as a microscopic solenoid, transformer, or pickup coil. In these applications there is the possibility of coolant flowing through the center of the hollow coils to remove heat.

If more than one layer of coils is required, such as in some solenoid and transformer applications, the overwrapped fiber can be wound back on itself as described above. Of course, for electrical applications such as these, the coil layers need to be insulated from one another. This can be accomplished by depositing a layer of insulation between the coil layers. Alternatively, one can wind either a conductive fiber with an insulating layer or a fiber that has an inner conductive layer and an outer insulative layer. Obviously, the conductive fiber would not be removed while the fiber with the two coatings could be removed.

The coil formed by this technology can also function as a spring and be used as a force or pressure sensor. This coil spring can be either hollow or filled. The spring constant can be controlled by varying the diameter of the coil, the diameter of the coated fiber, the spacing of the coils, the material of the fiber coating, the thickness of the coating, and whether the overwrapped fiber is removed or not.

Figure 8:
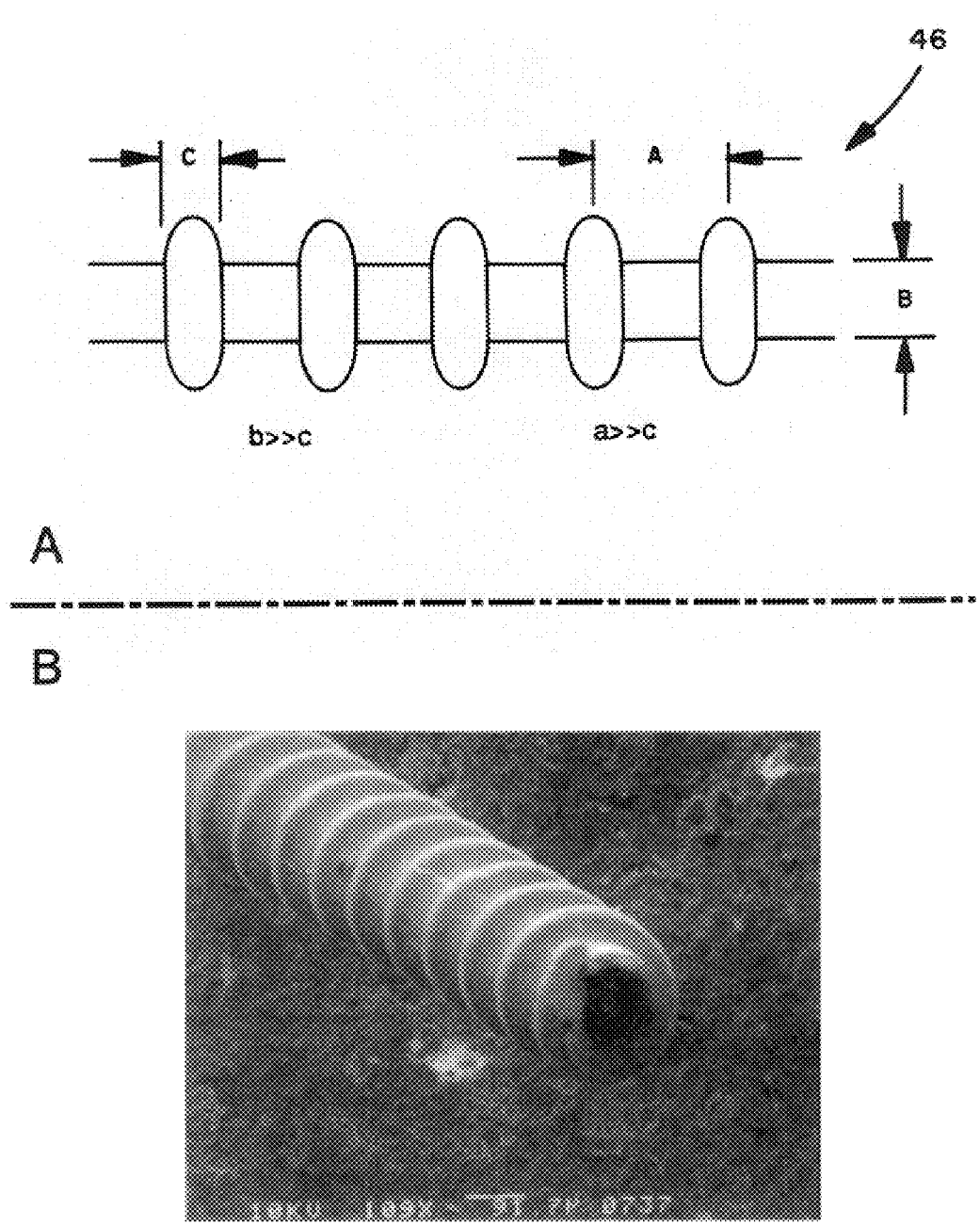
FIG. 8A illustrates a side view of wrapped bellows.
FIG. 8B illustrates (by photo) wrapped bellows.

If the fiber core diameter and overwrap fiber spacing are considerably larger than overwrap fiber diameter, the microtube resulting after coating both the overwrapped and the fiber core together and then removing both fibers will resemble a microbellows 46, FIG. 8A. A photograph of a bellows fabricated by this technique is shown in FIG. 8B. Of course, this bellows could also be manufactured by the other means discussed above. For example, material could be added to the core to form the fins, material could be removed from the core to form the depressions between the fins, or a technique such as embossing with a hot wire could be used. Obviously, for this simple structure many other techniques could also be employed.

There are numerous variations to the simple procedure of winding, coating, and fiber removal. Three such variations involve changing the core or overwrapped fiber cross-sectional-shape, coating sequences, and method of over-wrapping are given below.

Figure 9:
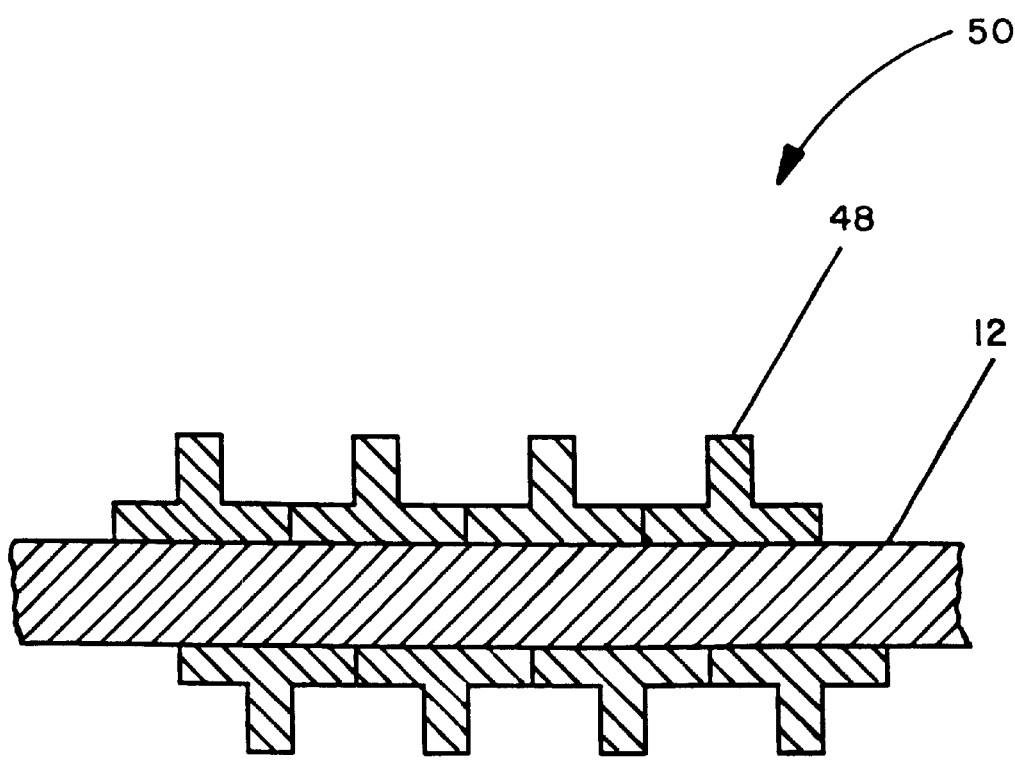
FIG. 9 illustrates a micro-threaded screw.

A variation of the helical winding pattern mentioned above is to employ noncircular overwrap fibers and/or a noncircular fiber core. For example in FIG. 9, if a trilobal overwrap fiber 48 is wound tightly enough around a circular fiber core 12, the trilobal fiber will deform into the shape of a "T". By spacing the "T" overwraps such that there are no gaps in between, a threaded screw 50 is precisely formed. It can have either right-handed or left-handed thread. Depending on the application, core and overwrap fibers may or may not be removed after coating. In the case of a screw they would probably be retained whereas in the case of a bellows they would be removed as with most examples discussed, this screw mandrel can also be fabricated in a number of ways. For example, a rectangular bead of material could be continuously extruded onto the fiber core surface or material could be removed from the periphery of the fiber core to produce rectangular depressions.

EXAMPLE 2

In addition to changing the cross-sectional shape of the overwrapping fiber it is also possible to coat the fiber core 12 (FIG. 10A) with a layer 52 before wrapping it with one or more overwrap fibers 10, and then coating it again with a second layer 54. Once the fiber core 12 and all overwrap fibers 10 have been removed, a microtube device 56 is formed that consists of a hollow helical channel wound around a hollow core tube. Such a device is presented in FIG. 10B. This process can be repeated to give as many layers of helical overwrap channels as desired. The two separate coating procedures and materials used do not have to be the same, and more than one coating can be employed in each. Also, noncircular core and/or overwrap fibers can be employed providing correspondingly shaped-core tubes and/or helical overwrap channels. An example of this is to employ a threaded-screw microtube 50 as the fiber core, and then overwrap circular fibers in the screw threads. FIG. 11 illustrates such a microtube device 58 once both core and overwrap coatings have been applied, and both core and overwrap fibers have been removed.

Figure 10:
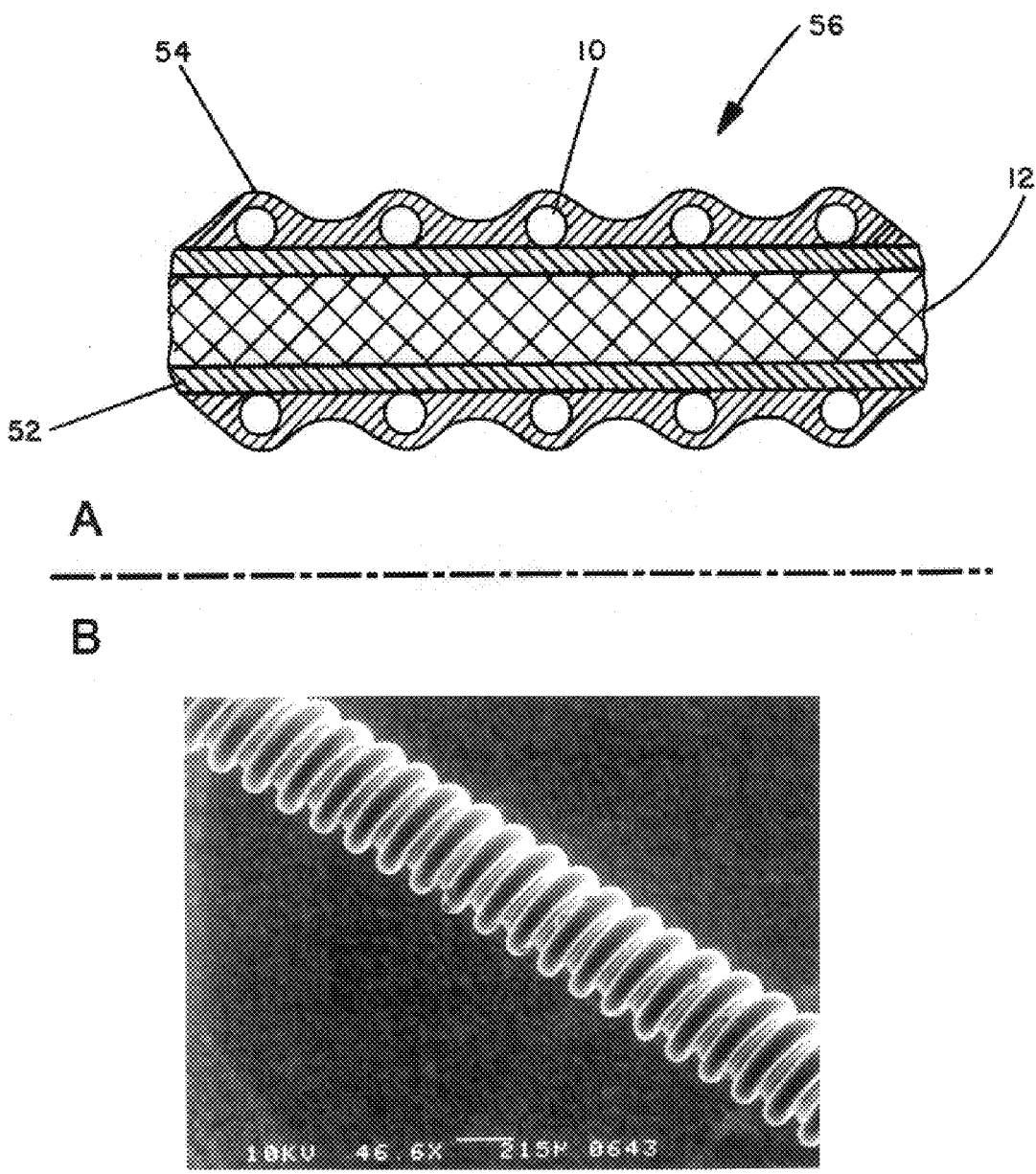
FIG. 10A illustrates a central microtube having a layer microtube wrapped about such.
FIG. 10B illustrates (by photo) a heat exchanger.
Figure 11:
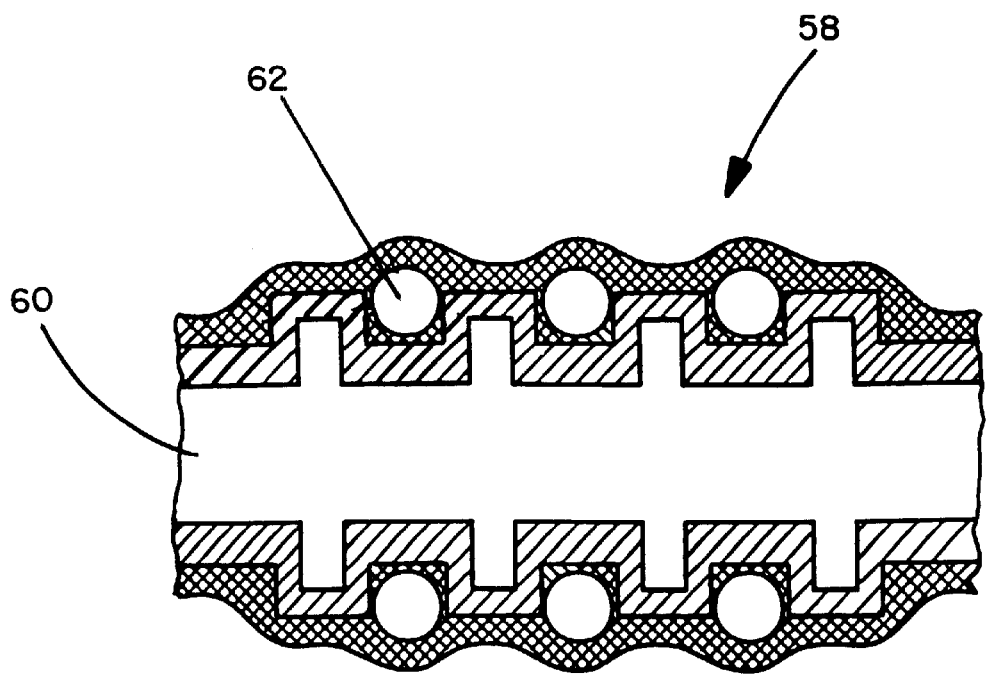
FIG. 11 illustrates a microtube threaded screw having a single channel wrapped thereabout and coated.
Figure 11:
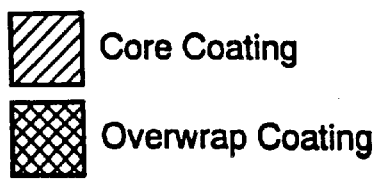

Most chemical or mechanical engineers will readily identify FIGS. 10 and 11 as heat exchangers, capable of being utilized in either co-current flow or counter-current flow situations. For example, in FIG. 11 fluid would flow in channel 60 and a second fluid could flow in the helical channel 62. An immediate application certainly exists in the cooling of high-power-density electronic microcircuits. These or similar configurations of microtubes can also be employed as microreactors for chemical synthesis. Again, any of the other techniques used to deposit material on, remove material from, or move material on the periphery of the fiber core can be used to form these structures.

FIGS. 10 and 11 offer a good example of the versatility of the present technology. That is, by making only minor changes in processing, completely different products can be fabricated. For example, in FIG. 10 if only the fiber core is removed and not the overwrapping fiber, a microtube with a reinforcement fiber in the wall will result. Obviously, more than one overwrapping pass can be made or multiple fibers can be wrapped producing a braiding in the tube wall.

EXAMPLE 3

Figure 12:
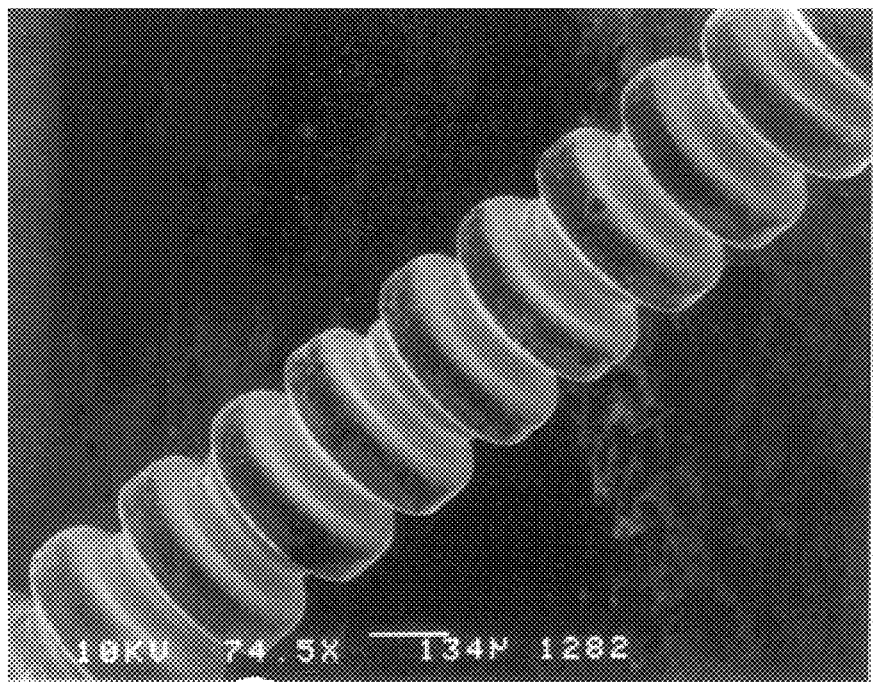
FIG. 12 illustrates a real circular bellows

If any technique discussed (ie. melt-processing, vapor-processing, embossing, ablation-processing, etc.) other than fiber overwrapping is employed, an actual bellows can be fabricated; i.e., zero pitch is achieved by forming a completely circumferential fin, on the fiber core at each repeat-unit location as seen in FIG. 12. (This is due to the fact that overwrapping by definition is a continuous process and therefore can only produce a continuous spiral fin. All the other techniques, in addition to being a continuous process, can also be non-continuous and thus only add, remove or move material in a purely circumferential manner at different locations on the fiber core surface.) This particular bellows was fabricated by selectively removing material from the fiber core, coating the fiber core, and then removing the fiber core. However, an equivalent structure can be produced by any technique that selectively adds material to the fiber core, selectively removes material from a layer on the fiber core, or selectively moves material such as embossing. The choice of techniques simply depends on the materials desired, the complex geometry to be fabricated, the ease of fabrication and the cost.

Figure 13:
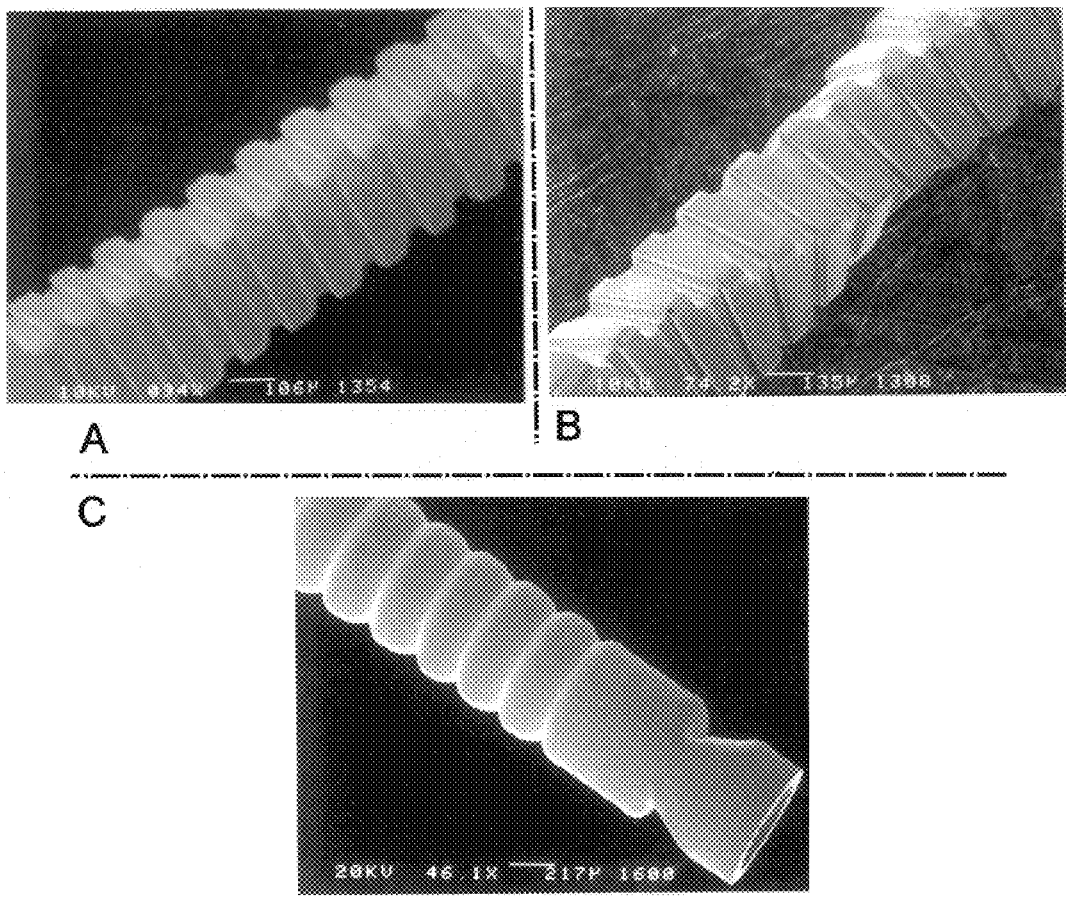
FIG. 13A illustrates a square bellows.
FIG. 13B illustrates a square bellows with a twist.
FIG. 13C illustrates a circular bellows with a dove-tail end

With any of these techniques, it is possible to produce bellows of any imaginable shape. FIG. 13 features two of the many possibilities. Shown are a square bellows (FIG. 13A) and a square bellows with a twist (FIG. 13B). Also shown is a round bellows with a dovetailed end (FIG. 13C) for attaching the bellows to a dovetailed channel on a micro-device. With the detailed end mounted on the micro-device and then sealed, the bellows is able to transport relatively high pressure gases and liquids.

Figure 14:
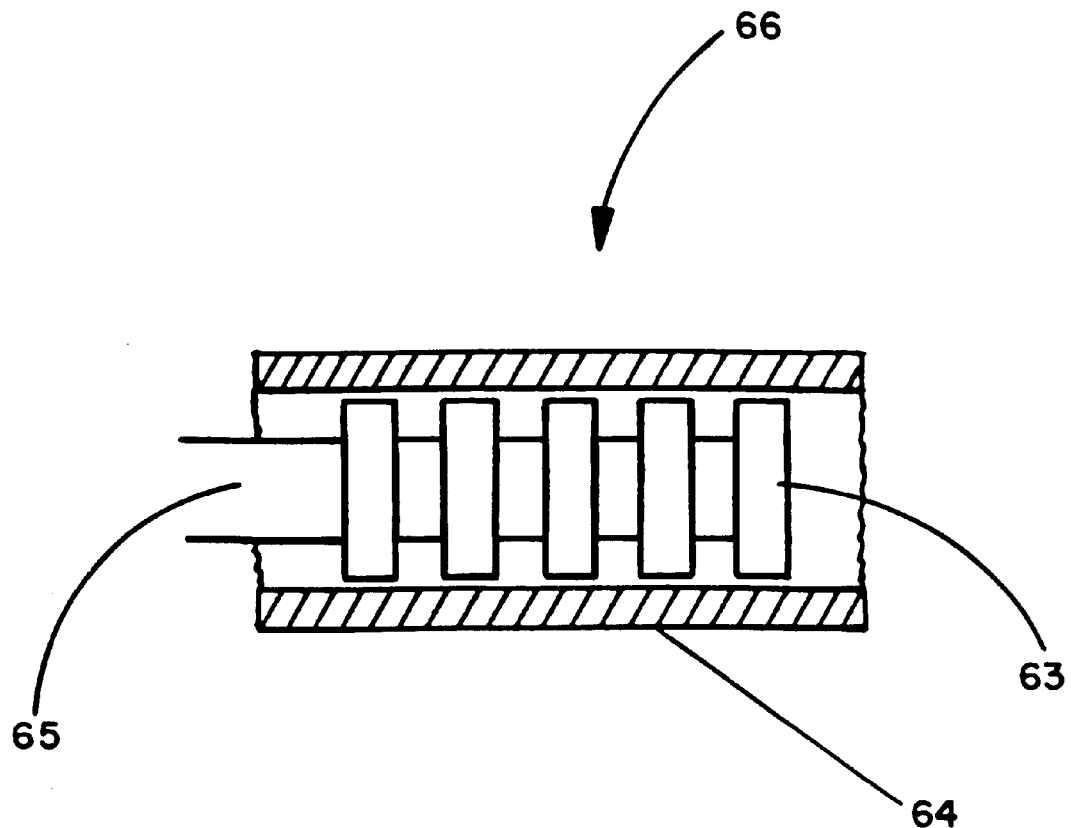
FIG. 14 illustrates a linear micro-actuator.
Figure 15:
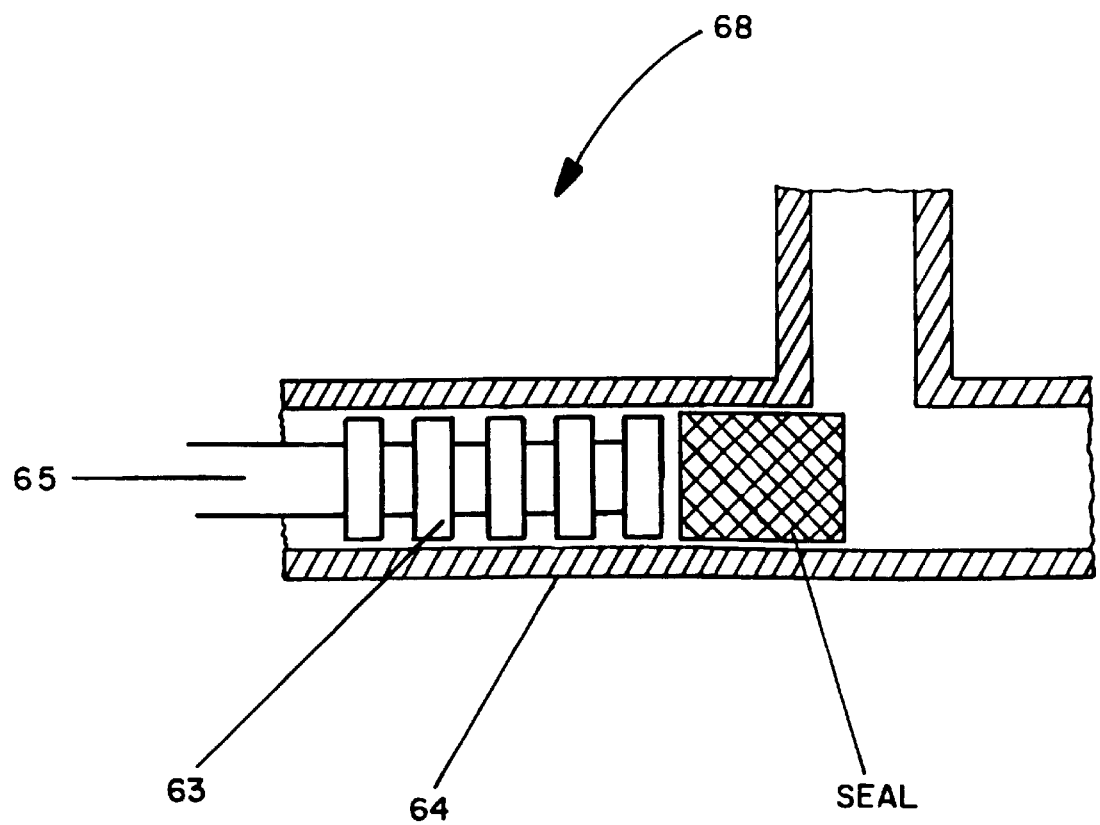
FIG. 15 illustrates a micro-valve.

Thus, bellows formed by this invention can be used as flexible couplings to carry gases or liquids between devices. A somewhat more sophisticated application at the micron level utilizes two of the properties of bellows; i.e., they are flexible and elongate under pressure 65 if one end is sealed. In FIG. 14, the bellows 63 is inserted into a rigid tube 64, bending is prevented and only one-dimensional motion is permitted. The resulting micro-actuator 66 is illustrated in FIG. 14. Obviously, an actuator utilizing micro-bellows can have as many degrees of freedom as there are bellows in the actuator and, in addition, the motion of these bellows can be nonlinear as a function of driving force. Many other uses for such a device can be envisioned. For example, the bellows sealed on one end and inserted in a rigid tube can also be used as a piston in a valve or pump. Even with clearance between the piston and the wall and without a ring or seal, this piston can be used to pump a non-wetting fluid. If it is desired to pump a fluid that wets the walls of the tube, a non-wetting droplet can be used as a seal according to Patent Application AFB 394. A micro-valve 68 in the half-open position is illustrated in FIG. 15.

Figure 16:
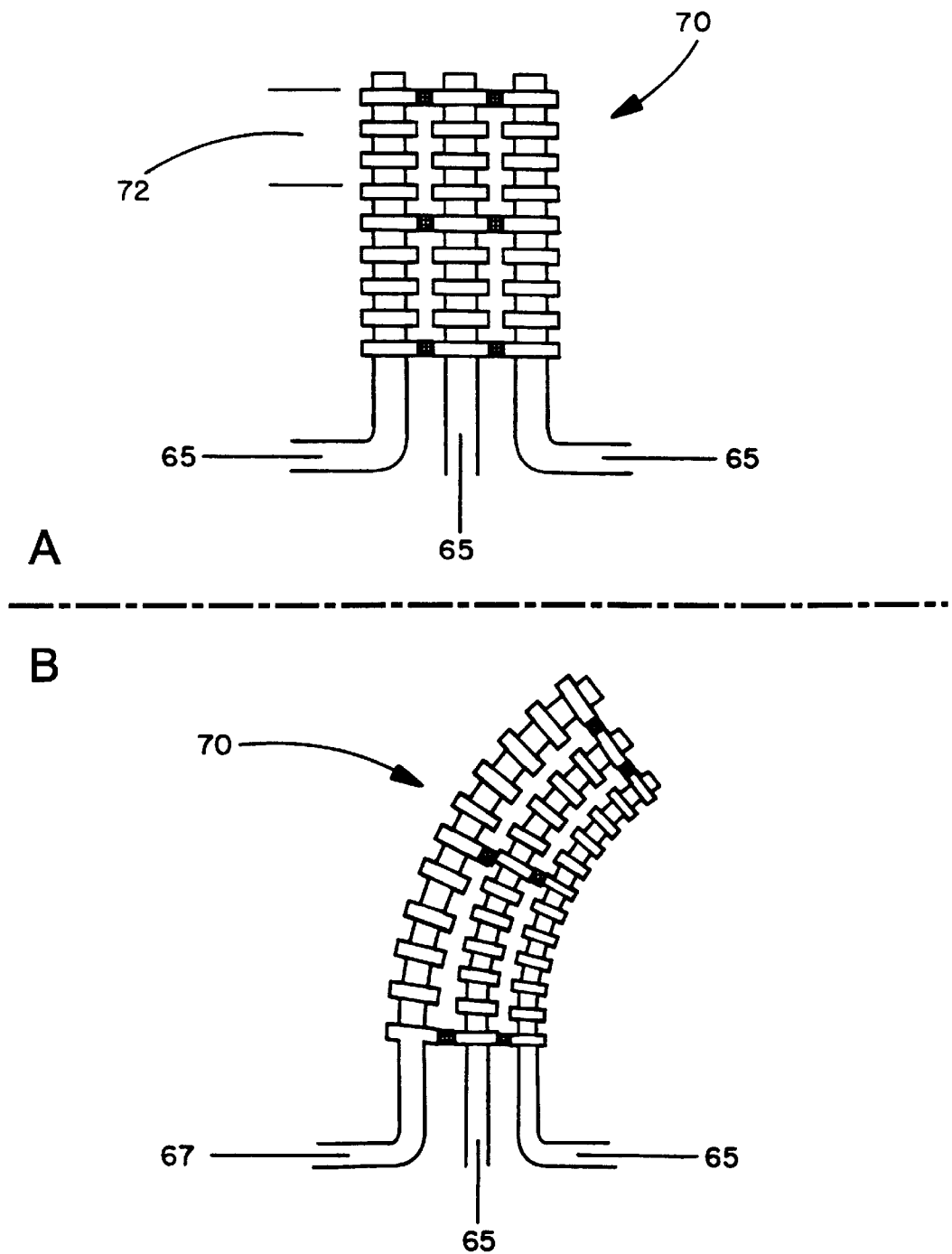
FIGS. 16A and 16B illustrate micro-fingers that are able to be pointed.
Figure 17:
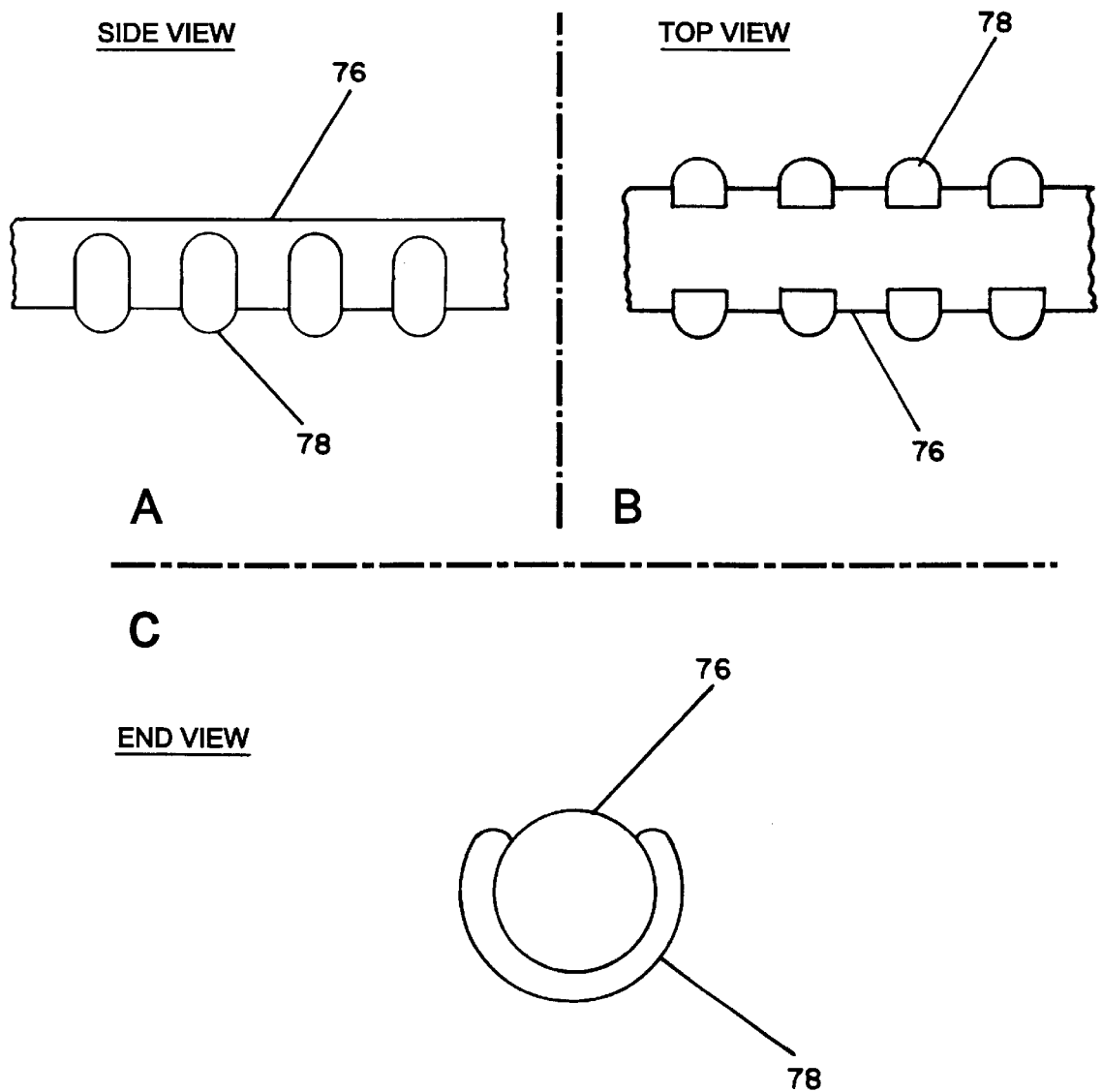
FIGS. 17A, 17B and 17C illustrate a bellows capable of bending motion.

If two or more bellows are attached together carefully at appropriate intervals 72 into a microbellows-assembly 70 as seen in FIG. 16A, applying a higher pressure 67 to one of them more than the others (FIG. 16B) will cause the remaining bellows in the assembly to deform in a direction away from the pressurized bellows. A similar response can be achieved by causing one bellows to shrink. In fact, a similar bending motion can also be achieved with only a single bellows. In this case, a bellows is fabricated so that over a significant length of the bellows there are smaller ribs 76 (or no ribs) on one segment of the periphery aligned along the axis (FIGS. 17A, 17B and 17C). If this "single finger" bellows 78 is then pressurized, it will bend toward the side that has the smaller ribs. For each of these designs, the overall effect can be thought of as similar to bending one's forefinger. A slight variation of the "single finger" bellows is to have the smaller rib section curve around the axis of the bellows instead of being linear along the axis. In this case the bellows will twist as well as bend. Obviously, the relative portion of twisting motion vs bending motion will be controlled by the pitch of the smaller ribs along the axis of the bellows.

Putting together two or more of these "micro-fingers" will result in a "micro-hand" which provides for manipulation at the micron level. Moreover, pressurizing or otherwise activating more than one bellows in an assembly will cause the entire assemble to change length as well as bend. By appropriately mounting microbellows-assemblies together, three-dimensional manipulation over relatively large distances at the micron level becomes feasible. Applications for these manipulators include positioning and working with specimens under microscopes, fabricating and/or repairing micro-electromechanical systems (MEMS), and microsurgery.

In any applications of the microbellows that is sealed on one or both ends, the elongation or contraction can take place in a number of ways. These include actuation using fluids inside the bellows (for example, hydrolytic, pneumatic, or electrokinetic actuation), as well as more exotic techniques involving a change in the length of the bellows material or a material in contact with the bellows. Thus, if the bellows is fabricated, for example, from a piezoelectric material, a magnetostrictive material, an electrostrictive material or a shape-memory alloy, the length can be changed by applying electrical, magnetic, or thermal energy. Obviously, the bellows need not be closed on either end to utilize these more exotic techniques.

It was stated in Example 1 that after the coil was coated, it was possible to leave the coated-fiber core in place to strengthen the coil. Obviously this is different technology than has been described in previous microtube patent applications. Microtube technology by definition forms a tube by removing a core consisting of a fiber or microscopic object of high aspect ratio from at least one coating placed on it. It should be noted that the process to remove the core can not adversely affect the at-least-one coating forming the tube wall. However, if the core is not removed or if one or more coatings are selectively removed leaving the core and at least one coating, an entirely new class of devices can result. For example, multi-layered-fiber coatings can be useful in the fabrication devices such as those that have an annular volume. This and many other devices can be made by applying multiple coatings to a core, complex mandrel, or sequential complex mandrel and then selectively, partially or completely, removing some of the layers leaving behind other layers and even, in some cases, the core, complex mandrel, or sequential complex mandrel. Of course, the core or complex mandrel can also be partially or completely removed.

By way of example, a fiber can be coated with two layers. If the layer closest to the fiber is preferentially removed, a device with an annulus would result with the annular volume contained between the original fiber and the outer coating. Of course, there would need to be some sort of axial and/or circumferential rib structure on the fiber mandrel to support the outer coating and keep the annulus open. As in most devices, this can be accomplished in a number of ways. A few will be given.

EXAMPLE 5

Figure 18:
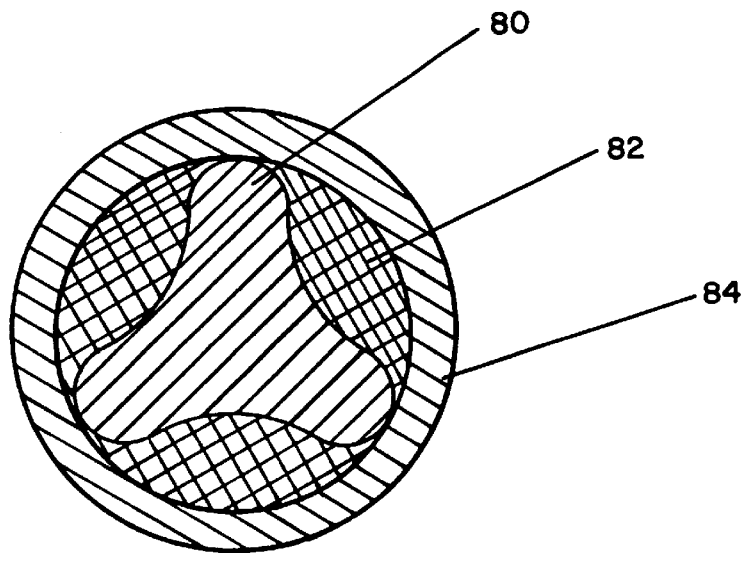
FIGS. 18A through 18H illustrate the manufacture of devices having an annulus.
Figure 18:
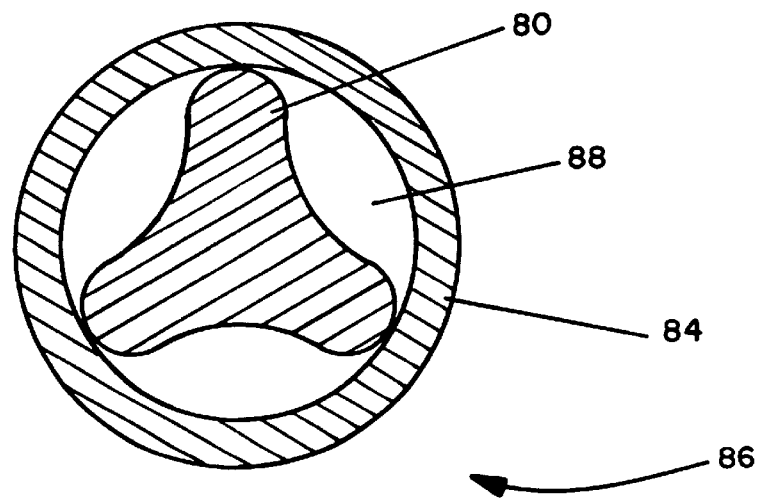
Figure 18:
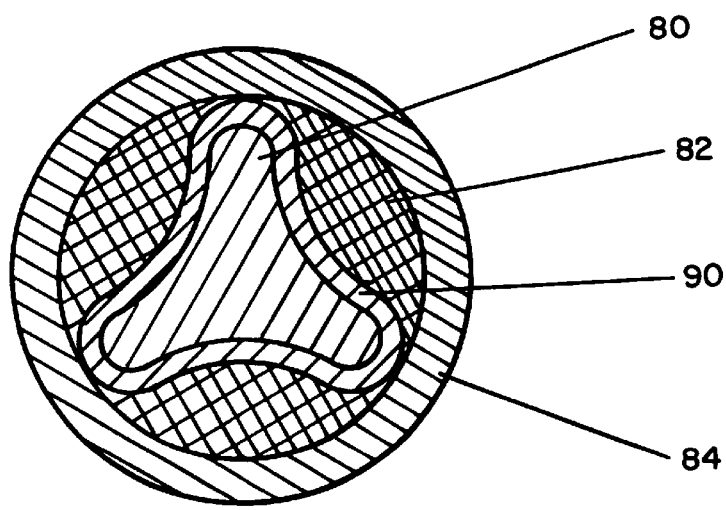
Figure 18:
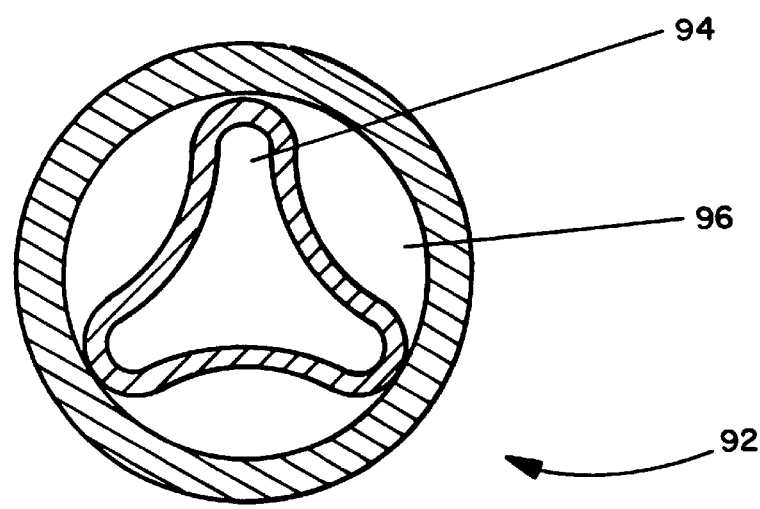
Figure 18:
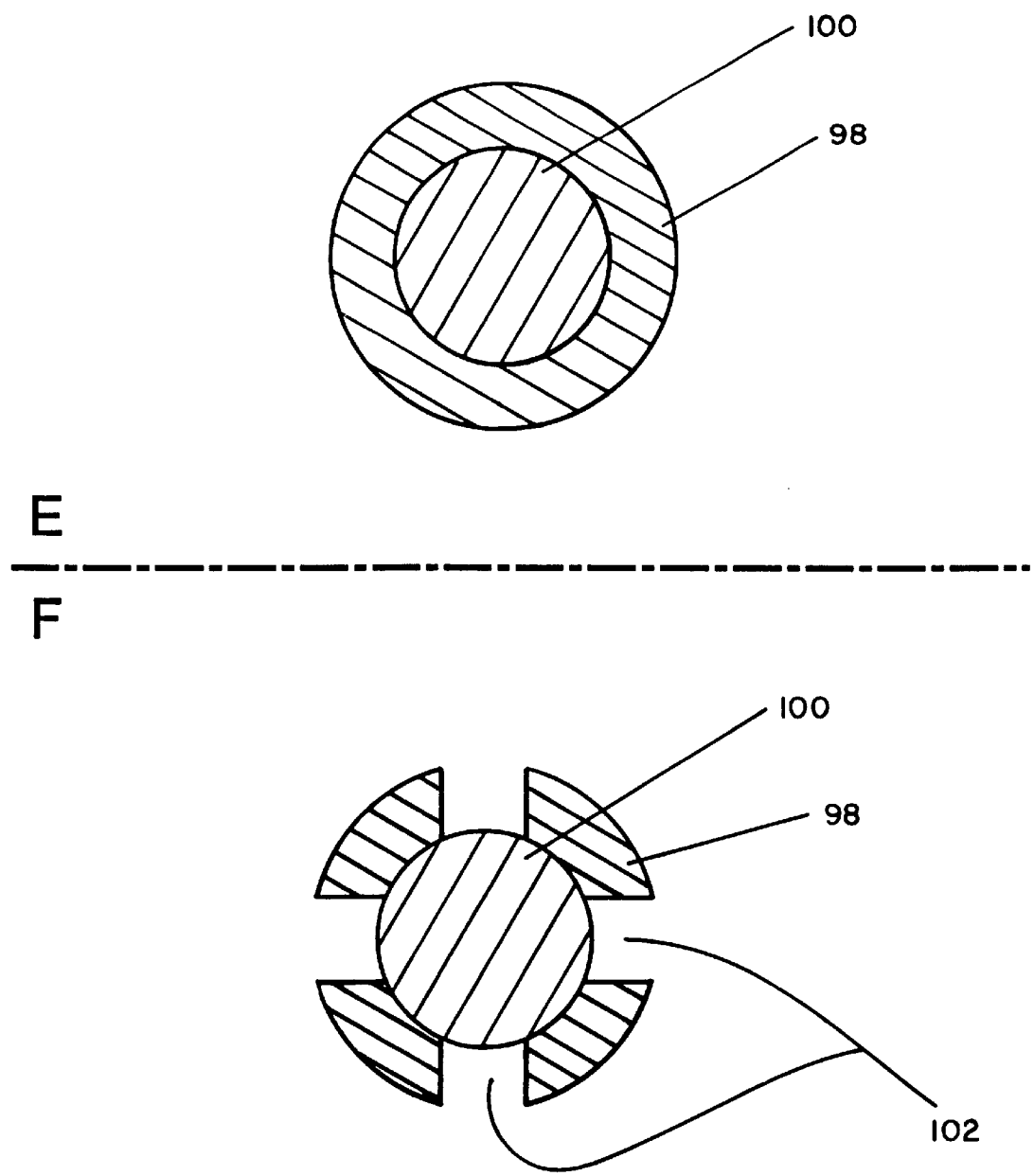
Figure 18:
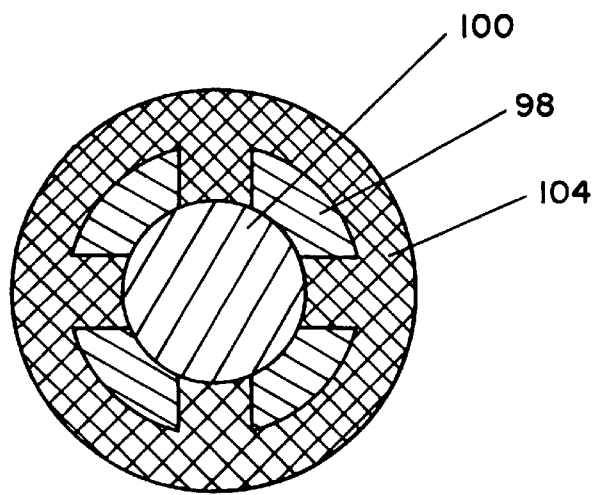
Figure 18:
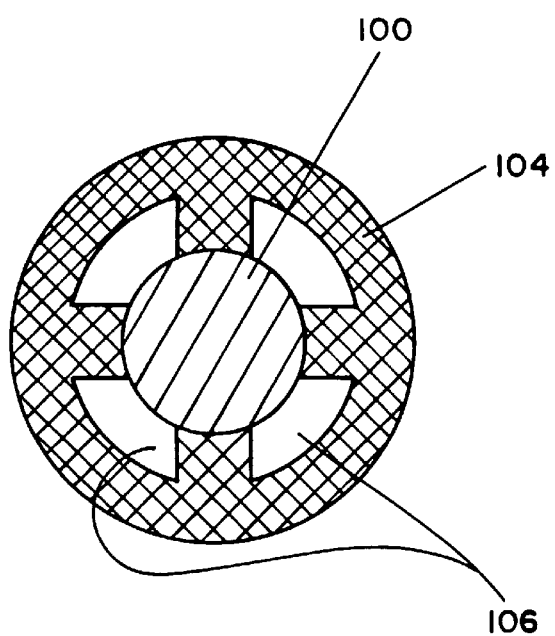

A simple example of the fabrication of this type of device is to start with an extruded fiber with ribs such as a trilobal fiber 80 in FIG. 18A. Using a multi-axis fabrication device, material 82 of a different type than the fiber can be added axial along the fiber filling the volume between the ribs. It should be noted that material 82 must be able to be removed by a process that does not remove the fiber 80. This complex augmented mandrel is then coated with another material 84 different than the material between the ribs 82 and not removed by a process used to removed the material 82 between the ribs. When the material between the ribs 82 is removed (FIG. 18B) a structure 86 with an annular volume 88 results. If the fiber core 80 has first been coated with a conformal layer 90 (FIG. 18C) before the material 82 is placed between the ribs and the coating 84 has been applied, when the fiber core 80 and material 82 are removed, a device 92 (FIG. 18D) with a central volume 94 as well as a concentric annulus 96 results. This tube within an annulus would prove useful in the fabrication of a counterflow heat exchanger or injectors, for example.

Obviously, there are numerous other ways to fabricate these annular structures. For example, to form a structure such as the annular structure 92, a rather thick coating 98 could be applied to a round fiber 100 (FIG. 18E). (It is necessary that techniques used to remove coating 98 not affect fiber 100.) The coating 98 is then partially removed or moved from locations 102 corresponding to the volumes between the rib structures needed to support the annulus (FIG. 18F). A second coating 104, which is not affected by techniques to remove coating 98, is placed on top of coating 98 filling all voids (FIG. 18G). When coating 98 is completely removed, voids 106 (FIG. 18H) result forming the annulus.

Figure 19:
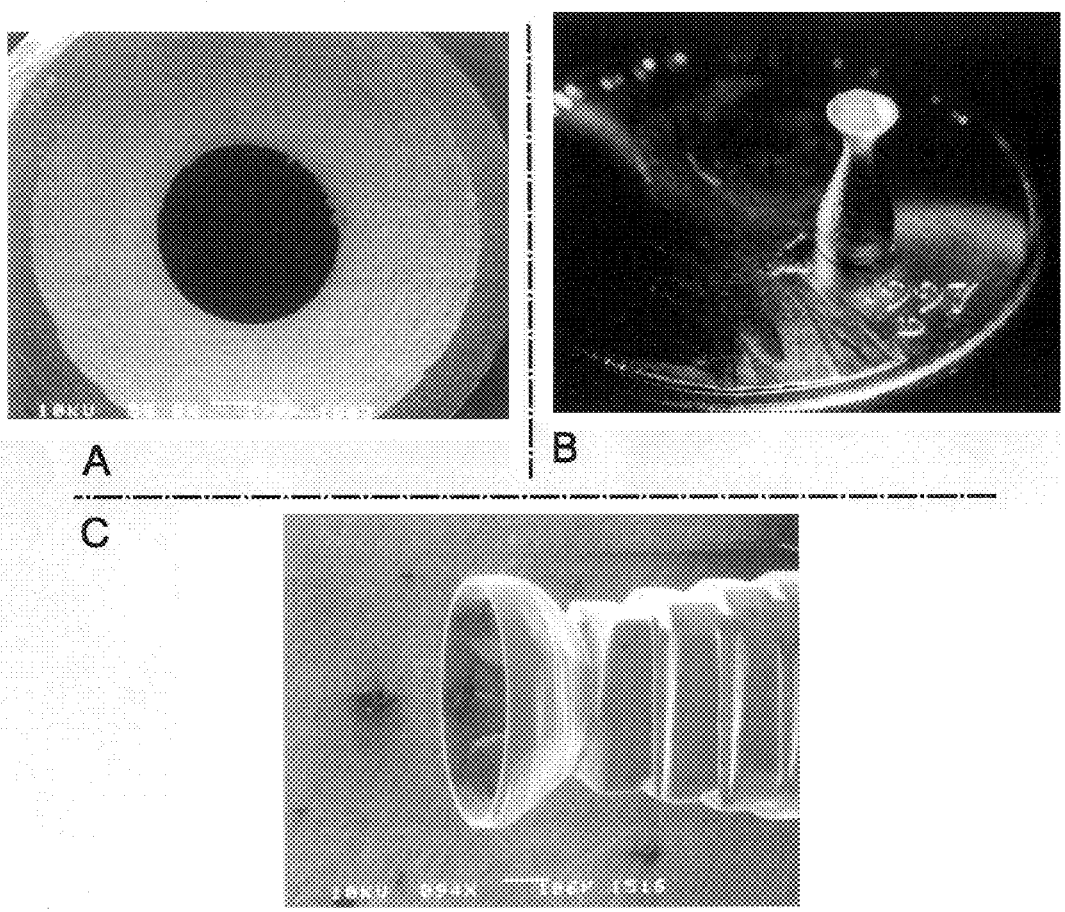
FIG. 19A illustrates a microscopic nozzle.
FIG. 19B illustrates the rocket nozzle for micro-thruster on a penny.
FIG. 19C illustrates a micro-camera bellows with a lens shade.

As should be apparent, a myriad of axial topographies on the micron scale leading to numerous micro-devices can be made using this invention. (A micro-rocket nozzle and a micro-camera bellows with a lens shade with interior dimensions of ~200 microns are shown by way of example in FIGS. 19A, 19B and 19C). Using the various techniques to add material to, subtract material from, move material on, modify the radial dimensions of, or wrap material around the core, either alone or in combination, results in very complex mandrels for the fabrication of microtube devices. For example, using melt processing more than one bead can be placed immediately next to another, or on top of another during a subsequent step of mandrel fabrication, to achieve whatever geometry is desired. This complex mandrel can then be "machined" to produce even a more complex mandrel. If you add to these capabilities, the possibility of starting with a mandrel of any cross-sectional shape, practically any complex-shaped mandrel can be fabricated.

Clearly, many modifications and variations of the present invention are possible in light of the above teachings and it is therefore understood, that within the inventive scope of the inventive concept, the invention may be practiced otherwise then specifically claimed.

What is claimed is:

1. A method of forming a microtube with a wall containing passages comprising:

providing a core, placing at least one coating on said core, forming a complex over-wrapped mandrel on a microwinding device by over-wrapping at least one threadlike component about the coated core, coating said complex over-wrapped mandrel with at least one layer of material to produce a coated complex mandrel and removing said core and said over-wrapped threadlike component, to produce a microtube containing wall passages.

2. A method of forming a microtube device a defined in claim 1 in which the core consists of at least one microscopic object with a high aspect ratio of length to diameter or at least one fiber with a cross-sectional dimension in the range of about 1 to 1000 microns.

3. A method of forming a microtube device as defined in claim 1 in which the at least one threadlike component consists of at least one microscopic object with high aspect ratio or at least one fiber with a cross-sectional dimension in the range of about 1 to 1000 microns.

4. A method of forming a microtube device as defined in claim 1 further including depositing at least one coating on said at least one overwrapping threadlike component before overwrapping said at least one overwrapping threadlike component on said coated core.

5. A method of forming a microtube device as defined in claim 1 wherein said at least one overwrapping fiber is made of polyetherimide.

6. A method of forming a microtube device as defined in claim 1 in which the surface of said at least one overwrapping threadlike component is melted just before being wrapped on said coated core to form a melt-bond with said coated core.

7. A method of forming a microtube device as defined in claim 1 in which the overwrapping threadlike component is comprised of at least one previously fabricated component selected from the group consisting of a complex mandrel, a coated complex mandrel and a coated complex mandrel from which the core, or complex mandrel and/or at least one coating has been removed; said previously fabricated component having been fabricated by process selected from the group consisting of changing the radial dimensions of a fiber core, overwrapping a core, adding material to a fiber core, removing material from a fiber core, moving material on a fiber core and a combination thereof.

8. A method of forming a microtube device as defined in claim 1 further including overwrapping at least one threadlike component on top of the coated complex overwrapped mandrel.

9. A method of forming a microtube device as defined in claim 8 including adding at least one additional coating on top of the at least one threadlike component overwrapping the coated complex overwrapped mandrel.

10. A method of forming a microtube device as defined in claim 9 further including removing at least one threadlike component from its coating after it has been overwrapped on top of the coated complex overwrapped mandrel.

11. A method for forming a macro-coil of a tubular threadlike component comprising:

providing a core and a threadlike component, placing a coating on said threadlike component to form a coated threadlike component, forming a complex overwrapped macro-mandrel on a winding device by overwrapping at least one of said coated threadlike component about said core;

removing said core from said macro-mandrel to produce at least one free-standing macro-coil of coated threadlike component and removing at least one threadlike component from said coating to produce a macro-coil of tubular threadlike component.

12. A method of forming a macro-coil of tubular threadlike component as defined in claim 11 in which the core consists of an object with a cross-sectional dimension in the range of about 1,000–25,000 microns.

13. A method of forming a macro-coil of tubular threadlike component as defined in claim 11 in which the overwrapping threadlike component consists of a microscopic object with high aspect ratio or at least one fiber with a cross-sectional dimension in the range of 1–1000 microns.

14. A method of forming a macro-coil of threadlike component as defined in claim 11 in which the overwrapping threadlike component is comprised of at least one previously fabricated component selected from the group consisting of a complex mandrel, a coated complex mandrel, and a coated complex mandrel from which the core or mandrel and/or at least one coating has been removed; said previously fabricated component having been fabricated by a process selected from the group consisting of changing the radial dimensions of a fiber core, overwrapping a core, adding material to a fiber core, removing material from a fiber core, moving material on a fiber core and a combination thereof.

15. A method of forming a macro-coil of tubular threadlike component comprising:

providing a core and a threadlike component, forming a complex overwrapped macro-mandrel on a winding device by overwrapping said threadlike component about said core;

removing said core from said macro-mandrel to produce at least one free-standing macro-coil of threadlike component;

placing a coating on the threadlike component and removing said threadlike component from said coating to produce a macro-coil of tubular threadlike component.

16. A method of forming a macro-coil of threadlike component as defined in claim 15 in which the core consists of an object with a cross-sectional dimension in the range of about 1000–25,000 microns.

17. A method of forming a macro-coil of threadlike component as defined in claim 15 in which the overwrapping threadlike component consists of a microscopic object with high aspect ratio or at least one fiber with a cross-sectional dimension in the range of 1–1000 microns.

18. A method of forming a macro-coil of threadlike component as defined in claim 15 in which the overwrapping threadlike component is comprised of at least one previously fabricated component selected from the group consisting of a complex mandrel, a coated complex mandrel, and a coated complex mandrel from which the core or. mandrel and/or at least one coating has been removed; said previously fabricated component having been fabricated by a process selected from the group consisting of changing the radial dimensions of a fiber core, overwrapping a core, adding material to a fiber core, removing material from a fiber core, moving material on a fiber core and a combination thereof.

* * * * *